US012564597B2

(12) United States Patent
Sames et al.

(10) Patent No.: US 12,564,597 B2
(45) Date of Patent: Mar. 3, 2026

(54) IBOGAINE ANALOGS AS THERAPEUTICS FOR NEUROLOGICAL AND PSYCHIATRIC DISORDERS

(71) Applicant: The Trustees of Columbia University in the City of New York, New York, NY (US)

(72) Inventors: Dalibor Sames, New York, NY (US); Vaclav Havel, Opava (CZ)

(73) Assignee: THE TRUSTEES OF COLUMBIA UNIVERSITY IN THE OF NEW YORK, New York, NY (US)

( * ) Notice: Subject to any disclaimer, the term of this patent is extended or adjusted under 35 U.S.C. 154(b) by 770 days.

(21) Appl. No.: 17/909,302

(22) PCT Filed: Mar. 4, 2021

(86) PCT No.: PCT/US2021/020908
§ 371 (c)(1),
(2) Date: Sep. 2, 2022

(87) PCT Pub. No.: WO2021/178691
PCT Pub. Date: Sep. 10, 2021

(65) Prior Publication Data
US 2023/0102206 A1 Mar. 30, 2023

Related U.S. Application Data

(60) Provisional application No. 62/985,646, filed on Mar. 5, 2020.

(51) Int. Cl.
*A61K 31/55* (2006.01)
*A61K 31/135* (2006.01)
(Continued)

(52) U.S. Cl.
CPC ............ *A61K 31/55* (2013.01); *A61K 31/135* (2013.01); *A61K 31/137* (2013.01);
(Continued)

(58) Field of Classification Search
CPC .......... A61P 25/00; A61P 25/36; A61P 25/24; A61P 25/22; A61P 11/14; A61P 25/04;
(Continued)

(56) References Cited

U.S. PATENT DOCUMENTS 3,639,408 A 2/1972 Nagata
4,499,096 A 2/1985 Lotsof
(Continued)

FOREIGN PATENT DOCUMENTS

WO WO 1997/005869 A1 2/1997
WO WO 2013/112757 8/2013
WO WO 2014/170704 A1 10/2014

OTHER PUBLICATIONS

Zubaran (CNS Drug reviews vol. 6, No. 3, pp. 219-240) (Year: 2000).*
(Continued)

*Primary Examiner* — Savitha M Rao
(74) *Attorney, Agent, or Firm* — Gary J. Gershik

(57) ABSTRACT
The present invention provides a composition which comprises a compound which is a mixture of deuterium con-
(Continued)

taining and non-deuterium containing molecules having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site,
or a pharmaceutically acceptable salt of the compound, and methods of using the composition to treat pain, depressive disorders, mood disorders, anxiety disorders, opioid use disorders, and opioid withdrawal symptoms.

20 Claims, 4 Drawing Sheets

(51) Int. Cl.

| | |
|---|---|
| *A61K 31/137* | (2006.01) |
| *A61K 31/437* | (2006.01) |
| *A61K 31/4375* | (2006.01) |
| *A61K 31/4468* | (2006.01) |
| *A61K 31/451* | (2006.01) |
| *A61K 31/4535* | (2006.01) |
| *A61K 31/454* | (2006.01) |
| *A61K 31/485* | (2006.01) |
| *A61K 31/554* | (2006.01) |
| *A61P 25/16* | (2006.01) |
| *A61P 25/24* | (2006.01) |
| *A61P 25/36* | (2006.01) |

(52) U.S. Cl.
    CPC ........ *A61K 31/437* (2013.01); *A61K 31/4375* (2013.01); *A61K 31/4468* (2013.01); *A61K 31/451* (2013.01); *A61K 31/4535* (2013.01); *A61K 31/454* (2013.01); *A61K 31/485* (2013.01); *A61K 31/554* (2013.01); *A61P 25/16* (2018.01); *A61P 25/24* (2018.01); *A61P 25/36* (2018.01)

(58) Field of Classification Search
    CPC ........ A61P 25/16; A61P 25/30; C07D 471/14; C07D 471/20; C07D 471/18; C07D 487/04; C07D 487/18; C07D 491/048; C07D 491/147; C07D 491/18; C07D 495/04; C07D 495/18; C07D 495/22; A61K 31/4375; A61K 45/06; A61K 31/437; A61K 31/55; A61K 2300/00; A61K 31/438; A61K 31/485; A61K 31/135; A61K 31/137; A61K 31/4468; A61K 31/451; A61K 31/4535; A61K 31/454; A61K 31/554; A61K 31/551
    See application file for complete search history.

(56) References Cited

U.S. PATENT DOCUMENTS

| | | | | |
|---|---|---|---|---|
| 5,152,994 | A | * 10/1992 | Lotsof | .................... A61K 31/55 424/463 |
| 5,616,575 | A | 4/1997 | Efange | |
| 8,741,891 | B1 | 6/2014 | Mash | |
| 8,940,728 | B2 | 1/2015 | Mash | |
| 9,045,481 | B2 | 6/2015 | Mash | |
| 9,561,233 | B2 | 2/2017 | Friedhoff | |
| 9,617,274 | B1 | 4/2017 | Moriarty et al. | |
| 9,988,377 | B2 | 6/2018 | Sames | |
| 11,840,541 | B2 | 12/2023 | Kruegel | |
| 2015/0246055 | A1 | 9/2015 | Friedhoff | |

OTHER PUBLICATIONS

International Search Report issued May 26, 2021 in connection with PCT International Application No. PCT/US2021/020908.
Notification of Transmittal of the International Search Report and the Written Opinion of the International Searching Authority, or the Declaration issued May 26, 2021 in connection with PCT International Application No. PCT/US2021/020908.
Hearn et al. "Identification and Quantitation of Ibogaine and an o-Demethylated Metabolite in Brain and Biological Fluids Using Gas Chromatography-Mass Spectrometry: Journal of Analytical Toxicology". Oct. 1995 p. 427-434; p. 429, Figure 2.
Gallagher et al. "Identification and quantification of the indole alkaloid ibogaine in biological samples by gas chromatography-mass spectrometry" Biochemical Pharmacology. Jan. 6, 1995 (Jan. 6, 1995) vol. 49, p. 73-79; p. 73, Fig. 1, p. 74, right col, para 1, p. 75, Fig. 2, p. 77, Fig. 3.
Written Opinion of the International Searching Authority issued May 26, 2021 in connection with PCT International Application No. PCT/US2021/020908.
Paul, et al. "Synthesis of new series of iboga analogues", Tetrahedron Letters, vol. 52, No. 46, 2011, pp. 6166-6169.
Rodriguez et al. "A Single Administration of the Atypical Psychedelic Ibogaine or its Metabolite Noribogaine Induces an Antidepressant-like Effect in Rats", ACS Chem. Neurosci. Apr. 2020. 11, 11, pp. 1661-1672.
Layer et al. "Structurally modified ibogaine analogs exhibit differing affinities for NMDA receptors", European Journal of Pharmacology, 1996. 309, pp. 159-165.
Delorenzi et al. "In Vitro Activities of Iboga Alkaloid Congeners Coronaridine and 18-Methoxycoronaridine against Leishmania amazonensis", Antimicrobial Agents and Chemotherapy. 2002. pp. 2111-2115.
Kam et al. "Cytotoxic effects and reversal of multidrug resistance by ibogan and related indole alkaloids" Bioorganic and Medicinal Chemistry Letters, vol. 14, No. 17, Sep. 2004, pp. 4487-4489.

* cited by examiner

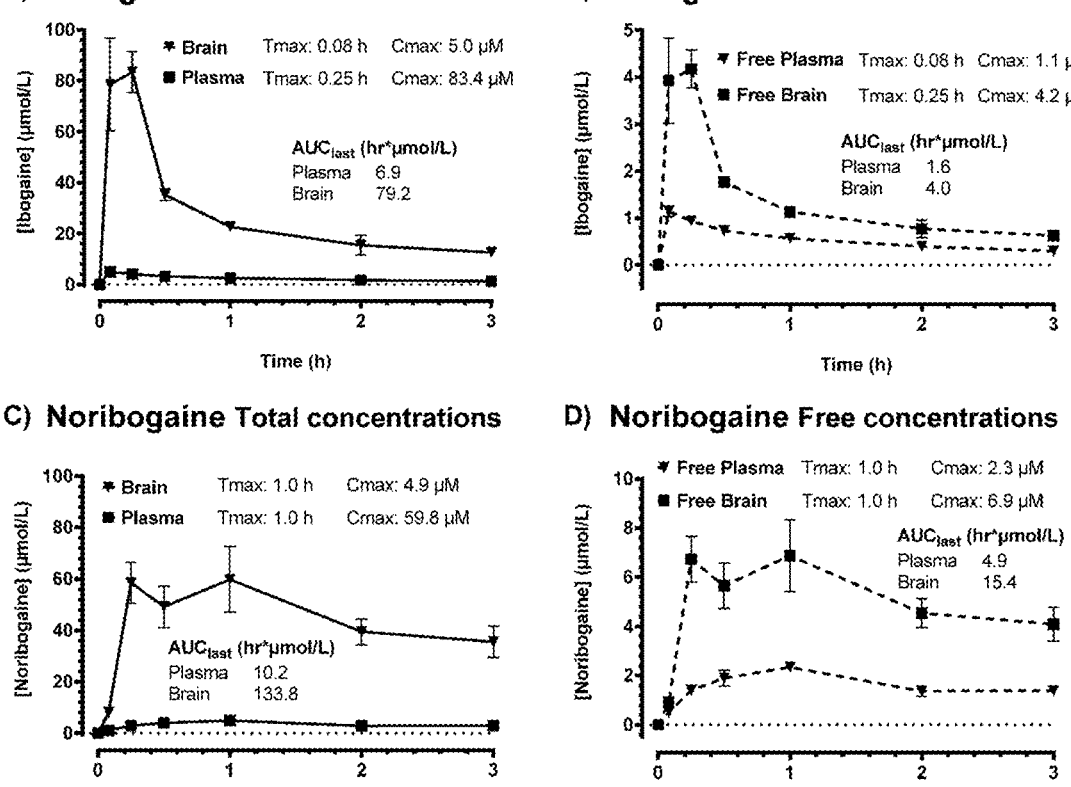
Fig. 2A-D

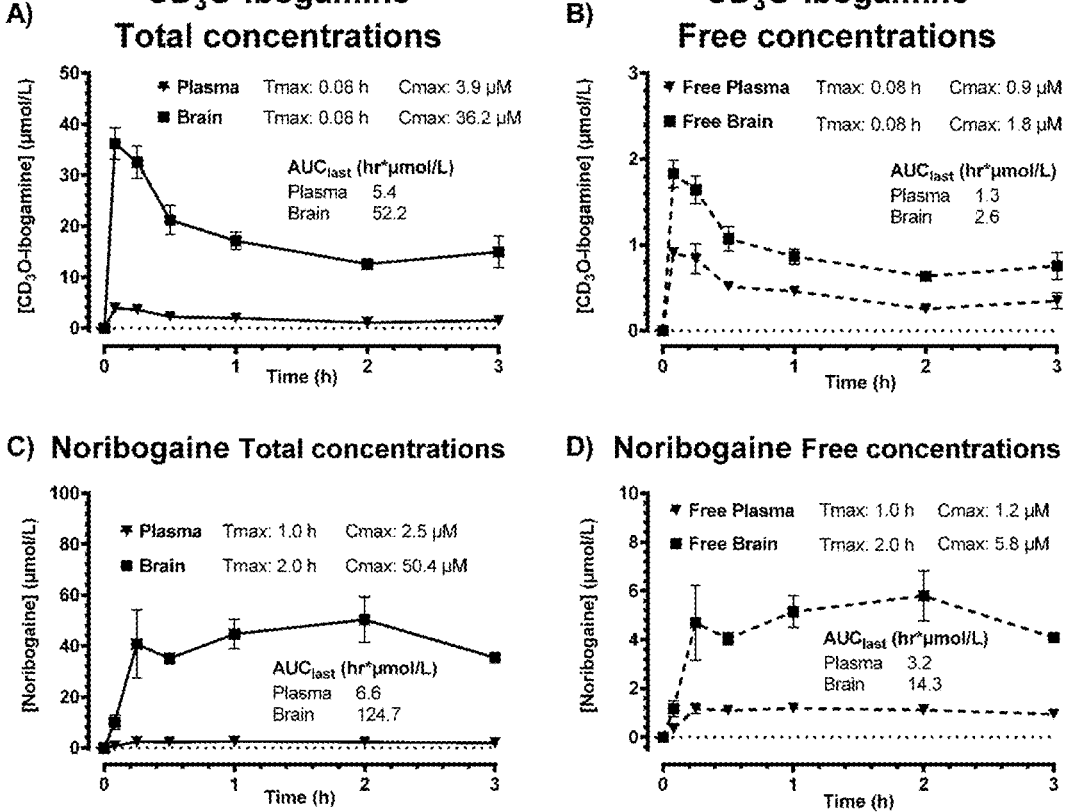
Fig. 3A-D

IBOGAINE ANALOGS AS THERAPEUTICS FOR NEUROLOGICAL AND PSYCHIATRIC DISORDERS

CROSS-REFERENCE TO RELATED APPLICATIONS

This application is a § 371 national stage of PCT International Application No. PCT/US2021/020908, filed Mar. 4, 2021, and claims the benefit of U.S. Provisional Application No. 62/985,646, filed Mar. 5, 2020, the entire contents each of which are hereby incorporated by reference into the subject application.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Ibogaine is the main indole alkaloid isolated from the root bark of the African shrub *Tabernanthe iboga* (Alper, K. R. 2001). It is an atypical psychedelic drug capable of inducing waking dream-like states (oneirogenic effects) and vivid memory recall and replay (Naranjo, C. 1973; Brown, T. K. et al. 2019). Anecdotal reports and open label case studies with volunteers seeking detoxification from heroin and cocaine indicated ibogaine's ability to interrupt the drug dependence phenotype via rapid and lasting relief of drug withdrawal symptoms and cravings (Alper, K. R. et al. 1999; Mash, D. C. et al. 2018; Schenberg, E. E. et al. 2014). Two recent open label observational clinical studies with subjects diagnosed with opioid dependence confirmed the earlier reports by showing a significant reduction of the withdrawal symptoms (3 days post-treatment) and an improvement of quality of life (up to 12 months) after a single ibogaine therapeutic session (Brown, T. K. et al. 2018; Noller, G. E. et al. 2018). One of these studies also reported a sustained antidepressant effect (evaluated up to 12 months post-treatment) (Noller, G. E. et al. 2018) consistent with the earlier observations of ibogaine's attenuation of depressive symptoms (Mash, D. C. et al. 2000).

Extensive preclinical work supports the clinical effects of ibogaine in rodent models of substance use disorders (SUDs), including attenuation of self-administration of opioids, cocaine, nicotine, and alcohol, as well as a reduction of opioid withdrawal symptoms in opioid-dependent animals (Glick, S. D. et al. 2001; Belgers, M. et al. 2016). In addition, it has been shown that noribogaine, ibogaine's major metabolite, exhibits a similar potency and efficacy profile in rodent models of SUDs, leading to the proposal of a mechanistic model where noribogaine contributes to the observed anti-SUD effects (Mash, D. C. et al. 2016).

SUMMARY OF THE INVENTION

The present invention provides a composition which comprises a compound which is a mixture of deuterium containing and non-deuterium containing molecules having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site,
or a pharmaceutically acceptable salt of the compound,
wherein in the mixture the proportion of molecules having deuterium at the at least one of $H_1$, $H_2$, $H_3$ $H_4$ or $H_5$ position is substantially greater than 0.0156% of molecules in the mixture.

The present invention also provides a composition which comprises a carrier and a compound having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site,
or a pharmaceutically acceptable salt of the compound.

BRIEF DESCRIPTION OF THE FIGURES

FIG. 2A-D: Total and unbound (free) plasma and brain concentrations of ibogaine and noribogaine detected after a single dose of ibogaine (40 mg/kg, i.p. administration). Error bars represent mean±SEM.

FIG. 3A-D: Total and unbound (free) plasma and brain concentrations of $CD_3O$-ibogamine and noribogaine detected after a single dose of $CD_3O$-ibogamine (40 mg/kg, i.p. administration). Error bars represent mean±SEM.

DETAILED DESCRIPTION OF THE INVENTION

Figure 1A:
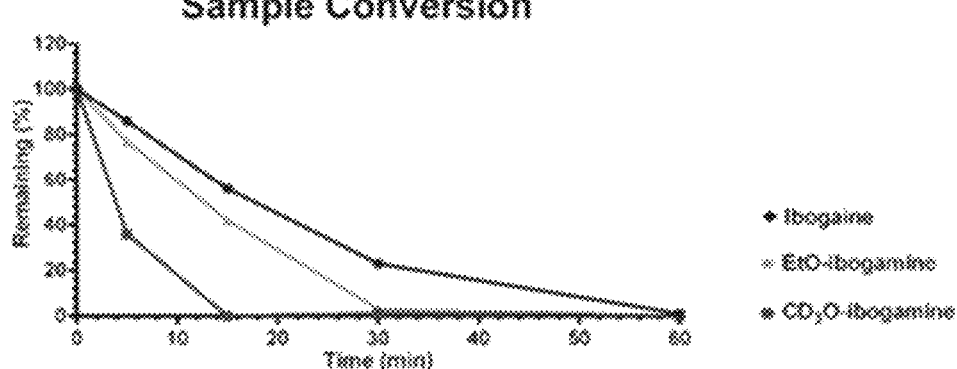
FIG. 1A: Conversion of ibogaine and its derivatives to noribogaine in rat liver microsomes.

The present invention provides a composition which comprises a compound which is a mixture of deuterium containing and non-deuterium containing molecules having the structure:

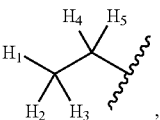

wherein $R_1$ is

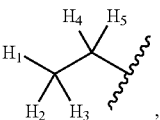

wherein at least one of $H_1$, $H_2$ or $H_3$ is a deuterium-enriched —H site, or

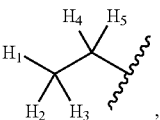

wherein at least one of $H_1$, $H_2$, $H_3$, $H_4$ or $H_5$ is a deuterium-enriched —H site,
or a pharmaceutically acceptable salt of the compound,
wherein in the mixture the proportion of molecules having deuterium at the at least one of $H_1$, $H_2$, $H_3$ $H_4$ or $H_5$ position is substantially greater than 0.0156% of molecules in the mixture.

In some embodiments, wherein $R_1$ is

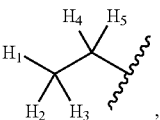

wherein at least one of $H_1$, $H_2$ or $H_3$ is a deuterium-enriched —H site.

In some embodiments, wherein each of $H_1$—$H_3$ are deuterium-enriched.

In some embodiments, wherein the proportion of molecules having deuterium at each of the $H_1$—$H_3$ positions is substantially greater than 90% of molecules in the composition.

In some embodiments, wherein two of $H_1$—$H_3$ are deuterium-enriched.

In some embodiments, wherein the proportion of molecules having deuterium at two of the $H_1$—$H_3$ positions is substantially greater than 90% of molecules in the composition.

In some embodiments, wherein one of $H_1$—$H_3$ is deuterium-enriched.

In some embodiments, wherein the proportion of molecules having deuterium at one of the $H_1$—$H_3$ positions is substantially greater than 90% of molecules in the composition.

In some embodiments, wherein $R_1$ is

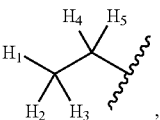

wherein at least one of $H_1$, $H_2$, $H_3$, $H_4$ or $H_5$ is a deuterium-enriched —H site.

In some embodiments, wherein each of $H_1$—$H_5$ are deuterium-enriched.

In some embodiments, wherein the proportion of molecules having deuterium at each of the $H_1$—$H_5$ positions is substantially greater than 90% of molecules in the composition.

In some embodiments, wherein each of $H_1$—$H_3$ are deuterium-enriched.

In some embodiments, wherein the proportion of molecules having deuterium at each of the $H_1$—$H_3$ positions is substantially greater than 90% of molecules in the composition.

In some embodiments, wherein each of $H_4$—$H_5$ are deuterium-enriched or one of $H_4$—$H_5$ is deuterium-enriched.

In some embodiments, wherein the proportion of molecules having deuterium at each of the $H_4$—$H_5$ positions is substantially greater than 90% of molecules in the composition, or the proportion of molecules having deuterium at one of the $H_4$—$H_5$ positions is substantially greater than 90% of molecules in the composition.

In some embodiments, wherein $R_1$ is other than

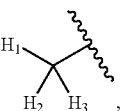

wherein each of $H_1$—$H_3$ are deuterium-enriched.

In some embodiments, wherein the compound has the structure:

-continued wherein D represents a deuterium-enriched —H site, or a pharmaceutically acceptable salt thereof.

In some embodiments, wherein the compound has the structure:

wherein D represents a deuterium-enriched —H site, or a pharmaceutically acceptable salt thereof.

The present invention also provides a composition which comprises a carrier and a compound having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site,
or a pharmaceutically acceptable salt of the compound.

In some embodiments, wherein $R_1$ is wherein at least one of $H_1$, $H_2$ or $H_3$ is a deuterium-enriched —H site.

In some embodiments, wherein each of $H_1$—$H_3$ are deuterium-enriched.

wherein D represents a deuterium-enriched —H site, or a pharmaceutically acceptable salt thereof.

In some embodiments, wherein the compound has the structure:

In some embodiments, wherein two of $H_1$—$H_3$ are deuterium-enriched.

In some embodiments, wherein one of $H_1$—$H_3$ is deuterium-enriched.

In some embodiments, wherein $R_1$ is wherein at least one of $H_1$, $H_2$, $H_3$, $H_4$ or $H_5$ is a deuterium-enriched —H site.

In some embodiments, wherein each of $H_1$—$H_5$ are deuterium-enriched.

In some embodiments, wherein each of $H_1$—$H_3$ are deuterium-enriched.

In some embodiments, wherein each of $H_4$—$H_5$ are deuterium-enriched or one of $H_4$—$H_5$ is deuterium-enriched.

In some embodiments, wherein $R_1$ is other than wherein each of $H_1$—$H_3$ are deuterium-enriched.

In some embodiments, wherein the compound has the structure:

-continued wherein D represents a deuterium-enriched —H site, or a pharmaceutically acceptable salt thereof.

In some embodiments, wherein the compound has the structure:

wherein D represents a deuterium-enriched —H site, or a pharmaceutically acceptable salt thereof.

In some embodiments, wherein the compound has the structure:

wherein D represents a deuterium-enriched —H site, or a pharmaceutically acceptable salt thereof.

In some embodiments, wherein the level of deuterium at any one of the deuterium-enriched —H sites of the compound is 20%-100%, 50%-100%, 70%-100%, 90%-100%, 97%-100%, or 99%-100%.

In some embodiments, wherein the level of deuterium at any one of the deuterium-enriched —H sites of the compound is no less than 50%, no less than 70%, no less than 90%, no less than 97% or no less than 99%.

In some embodiments, the composition further comprising a carrier.

In some embodiments, wherein the carrier is a pharmaceutically acceptable carrier.

In some embodiments, the composition further comprising a mu-opioid receptor agonist.

In some embodiments, the composition further comprising an opioid or opiate.

In some embodiments, wherein the opioid or opiate is morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil, buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c,f][1,2]thiazepin-11-yl)amino)heptanoic acid, 7-((3-iodo-6-methyl-5,5-dioxido-6,11-dihydrodibenzo[c,f][1,2] thiazepin-11-yl) amino)heptanoic acid, 5-((3-bromo-6-methyl-5,5-dioxido-6, 11-dihydrodibenzo[c,f][1,2]thiazepin-11-yl)amino) pentanoic acid or 5-((3-iodo-6-methyl-5,5-dioxido-6,11-dihydrodibenzo[c,f][1,2]thiazepine-11-yl)amino)pentanoic acid.

The present invention provides a method of altering the psychological state of a subject comprising administering to the subject the composition of the present invention comprising an effective amount of the compound so as to thereby alter the psychological state of the subject.

The present invention provides a method of enhancing the effect of psychotherapy in a subject comprising administering to the subject the composition of the present invention comprising an effective amount of the compound so as to thereby enhance the effect of the psychotherapy in the subject.

The present invention provides a method of inducing wakefulness or decreasing sleepiness in a subject comprising administering to the subject the composition of the present invention comprising an effective amount of the compound so as to thereby induce wakefulness or decrease sleepiness in the subject.

The present invention provides a method of decreasing the duration of REM sleep in a subject comprising administering to the subject the composition of the present invention comprising an effective amount of the compound so as to thereby decrease the duration of REM sleep in the subject.

The present invention provides a method of increasing energetic feelings in a subject comprising administering to the subject the composition of the present invention comprising an effective amount of the compound so as to thereby increase the energetic feelings in the subject.

The present invention provides a method of inducing a stimulating effect in a subject comprising administering to the subject the composition of the present invention comprising an effective amount of the compound so as to thereby induce the stimulating effect in the subject.

In some embodiments, the stimulating effect is a central stimulating effect.

In some embodiments, the stimulating effect is induced substantially free of undesired side-effects in the subject.

In some embodiments, the stimulating effect is induced without inducing an addictive effect in the subject to the compound.

In some embodiments, a use of the composition of the present invention comprising an effective amount of the compound as a stimulant.

The present invention provides a method of treating a subject afflicted with substance use disorder comprising administering to the subject the composition of the present invention comprising an effective amount of the compound so as to thereby treat the subject afflicted with the substance use disorder.

In some embodiments, wherein the substance use disorder is opioid use disorder, alcohol use disorder or stimulant use disorder.

The present invention provides a method of treating a subject afflicted with opioid withdrawal symptoms comprising administering to the subject the composition of the present invention comprising an effective amount of the compound so as to thereby treat the subject afflicted with the opioid withdrawal symptoms.

The present invention provides a method of treating a subject afflicted with a depressive disorder, a mood disorder, an anxiety disorder, Parkinson's disease, or traumatic brain injury administering to the subject the composition of the present invention comprising an effective amount of the compound so as to thereby treat the subject afflicted with the depressive disorder, the mood disorder, the anxiety disorder, Parkinson's disease, the traumatic brain injury.

The present invention provides a method of treating a subject afflicted with pain comprising administering to the subject the composition of the present invention comprising an effective amount of the compound and the opioid or opiate so as to thereby treat the subject afflicted with pain.

In some embodiments, wherein an effective amount of 10-1500 mg of the compound is administered to the subject.

The present invention further provides a method for systemic in vivo delivery of a first compound having the structure:

to a subject, the method comprising administering to the subject a composition which comprises a carrier and a second compound having the structure:

wherein R$_1$ is wherein at least one of H$_1$, H$_2$ or H$_3$ is a deuterium-enriched —H site, or wherein at least one of $H_1$, $H_2$, $H_3$, $H_4$ or $H_5$ is a deuterium-enriched —H site, or a pharmaceutically acceptable salt of the compound, so as to thereby deliver the first compound to the subject.

In some embodiments, the method wherein in vivo delivery of the first compound at a rate that is substantially less than the rate of delivery of the first compound resulting from administration of a composition which comprises a carrier and ibogaine.

In some embodiments, the method wherein $R_1$ is other than wherein each of $H_1$—$H_3$ are deuterium-enriched.

In some embodiments, the method wherein the compound has the structure:

or

-continued wherein D represents a deuterium-enriched —H site, or a pharmaceutically acceptable salt thereof.

In some embodiments, the method wherein the compound has the structure:

wherein D represents a deuterium-enriched —H site, or a pharmaceutically acceptable salt thereof.

In some embodiments, the method wherein the compound has the structure:

wherein D represents a deuterium-enriched —H site, or a pharmaceutically acceptable salt thereof.

In some embodiments, the method wherein the subject is a mammal.

In some embodiments, the method wherein the mammal is a human.

In some embodiments, the composition wherein one or more or all of $H_1$—$H_5$ are deuterium-enriched.

In some embodiments, the composition wherein $H_1$ is a deuterium-enriched —H site.

In some embodiments, the composition wherein $H_2$ is a deuterium-enriched —H site.

In some embodiments, the composition wherein $H_3$ is a deuterium-enriched —H site.

In some embodiments, the composition wherein $H_4$ is a deuterium-enriched —H site.

In some embodiments, the composition wherein $H_5$ is a deuterium-enriched —H site.

In some embodiments, wherein when the composition contains more than the naturally occurring number of molecules of the compound having deuterium at one or more sites then the composition is a deuterium-enriched composition.

In some embodiments, wherein the pharmaceutical composition is enriched in the compound that contains deuterium in place of —H.

In some embodiments, a pharmaceutical composition comprising the composition of the present invention wherein the carrier is a pharmaceutically acceptable carrier.

The present invention also provides a pharmaceutical composition which comprises a pharmaceutically acceptable carrier and a compound having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site,
or a pharmaceutically acceptable salt of the compound, In some embodiments, the composition wherein any one of $H_1$—$H_5$ is a deuterium-enriched —H site and the level of deuterium at the deuterium-enriched —H site of the compound is 0.02% to 100%.

In some embodiments, the composition wherein any one of $H_1$—$H_5$ is a deuterium-enriched —H site and the level of deuterium at the deuterium-enriched —H site of the compound is 20%-100%, 50%-100%, 70%-100%, 90%-100%, 97%-100%, or 99%-100%.

In some embodiments, the composition of wherein any one of $H_1$—$H_5$ is a deuterium-enriched —H site and the level of deuterium at the deuterium-enriched —H site of the compound is no less than 50%, no less than 70%, no less than 90%, no less than 97% or no less than 99%.

In some embodiments, the composition wherein the compound has the structure:

wherein D represents a deuterium-enriched —H site or a pharmaceutically acceptable salt thereof.

In some embodiments, the composition wherein the compound has the structure:

15

-continued wherein D represents a deuterium-enriched —H site or a pharmaceutically acceptable salt thereof.

In some embodiments, the composition wherein the compound has the structure:

wherein D represents a deuterium-enriched —H site or a pharmaceutically acceptable salt thereof.

In some embodiments of the composition, the composition wherein the compound has the structure:

16

-continued or a pharmaceutically acceptable salt thereof.

In some embodiments of the composition, the composition wherein the compound has the structure:

or a pharmaceutically acceptable salt thereof.

In some embodiments of the composition, the composition wherein the compound has the structure:

or a pharmaceutically acceptable salt thereof.

The present invention provides a composition which comprises a mixture of molecules each having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site, or a pharmaceutically acceptable salt of the compound, wherein the proportion of molecules of the compound having deuterium at the $H_1$—$H_5$ position is substantially greater than 0.0156% of molecules in the composition.

The present invention provides a composition which comprises a mixture of deuterium containing and non-deuterium containing compounds having the structure:

wherein $R_1$ is wherein at least one of $H_1$, $H_2$ or $H_3$ is a deuterium-enriched —H site, or wherein at least one of $H_1$, $H_2$, $H_3$, $H_4$ or $H_5$ is a deuterium-enriched —H site, or a pharmaceutically acceptable salt of the compound, wherein the proportion of molecules of the compound having deuterium at the $H_1$—$H_5$ position is substantially greater than 0.0156% of molecules in the composition.

In some embodiments of the composition, the composition wherein the deuterium containing compound has the structure:

, or

-continued or a pharmaceutically acceptable salt thereof.

In some embodiments of the composition, the composition wherein the deuterium containing compound has the structure:

or a pharmaceutically acceptable salt thereof.

In some embodiments of the composition, the composition wherein the deuterium containing compound has the structure:

or a pharmaceutically acceptable salt thereof.

In some embodiments of the above composition, a mixture of the deuterium containing compound and the non-deuterium containing compound in a ratio in a range of 1:4 to 4:1.

In some embodiments of the above composition, a mixture of the deuterium containing compound and the non-deuterium containing compound in a ratio in a range of 2:3 to 3:2.

In some embodiments of the above composition, a mixture of the deuterium containing compound and the non-deuterium containing compound in a ratio in a range of 1:1 to 2:1.

In some embodiments of the above composition, a mixture of the deuterium containing compound and the non-deuterium containing compound in a ratio in a range of 1:1 to 1:2.

In some embodiments of the above composition, a mixture of the deuterium containing compound and the non-deuterium containing compound in a ratio of 1:1, 2:1 or 1:2.

In some embodiments of the above composition, a mixture of $CD_3$O-ibogamine and ibogaine in a ratio in a range of 1:1 to 2:1.

In some embodiments of the above composition, a mixture of $CD_3$O-ibogamine and ibogaine in a ratio in a range of 1:1 to 1:2.

In some embodiments of the above composition, a mixture of $CD_3$O-ibogamine and ibogaine in a ratio of 1:1, 2:1 or 1:2.

In some embodiments of the above composition, a mixture of $CD_3$O-ibogamine and ibogaine in a ratio in a range of 1:1 to 3:1.

In some embodiments of the above composition, a mixture of $CD_3$O-ibogamine and ibogaine in a ratio in a range of 1:1 to 1:3.

In some embodiments of the above composition, the mixture is formed by combining the presynthesized deuterium containing compound with the corresponding presynthesized non-deuterium containing compound.

In some embodiments of the above composition, the mixture is formed in situ in the synthesis of the deuterium containing compound.

In some embodiments of the above composition, the mixture is formed by combining the presynthesized $CD_3$O-ibogamine with ibogaine.

In some embodiments of the above composition, the mixture is formed in situ in the synthesis of $CD_3$O-ibogamine.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 99% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 95% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 90% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 80% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 70% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 60% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 50% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 40% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 30% of molecules in the composition.

In some embodiments of any of the above compositions, wherein the proportion of molecules of the compound having deuterium at the $H_1$, $H_2$ and $H_3$, at the $H_4$ and $H_5$ or at the $H_1$, $H_2$, $H_3$, $H_4$ and $H_5$ position is greater than 20% of molecules in the composition.

In some embodiments of any of the above compositions, the compound wherein each of $H_1$—$H_5$ is a deuterium or a hydrogen.

In some embodiments of any of the above recited compounds, $H_1$—$H_5$ are each independently —H or a deuterium-enriched —H site.

In some embodiments of any of the above recited compounds, $H_1$—$H_5$ are each independently —H or -D.

In some embodiments of any of the above composition, the composition further comprising a carrier.

In some embodiments of any of the above composition, the composition wherein the carrier is a pharmaceutically acceptable carrier.

In some embodiments of any of the above compositions, the composition further comprising a mu-opioid receptor agonist.

In some embodiments of any of the above compositions, the composition further comprising an opioid or opiate.

In some embodiments of any of the above compositions, the composition further comprising morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c,f][1,2]thiazepin-11-yl)amino)heptanoic acid, 7-((3-iodo-6-methyl-5,5-dioxido-6,11-dihydrodibenzo[c,f][1,2] thiazepin-11-yl)amino)heptanoic acid, 5-((3-bromo-6-methyl-5,5-dioxido-6,11-dihydrodibenzo[c,f][1,2] thiazepin-11-yl)amino)pentanoic acid or 5-((3-iodo-6-methyl-5,5-dioxido-6,11-dihydrodibenzo[c,f][1,2] thiazepin-11-yl)amino)pentanoic acid.

In some embodiments of any of the above compositions, the composition further comprising any of the compounds disclosed in PCT International Publication Nos. WO 2015/138791, WO 2017/049158, WO 2018/170275 or WO 2020/037136, the contents of each of which are hereby incorporated by reference.

In some embodiments, a method of altering the psychological state of a subject comprising administering to the subject the composition of the present invention comprising an effective amount of the compound so as to thereby alter the psychological state of the subject.

In some embodiments, a method of enhancing the effect of psychotherapy comprising administering to the subject the composition of the present invention comprising an effective amount of the compound so as to thereby enhance the effect of the psychotherapy.

In some embodiments, a method of treating a subject afflicted with a depressive disorder, a mood disorder or an anxiety disorder, comprising administering to the subject the composition of the present invention comprising an effective amount of the compound so as to thereby treat the subject afflicted with the depressive disorder, the mood disorder or the anxiety disorder.

In some embodiments, the depressive disorder, the mood disorder or the anxiety disorder.

In some embodiments, a method of reducing opioid cravings in a subject afflicted with an opioid use disorder comprising administering to the subject the composition of the present invention comprising an effective amount of the compound so as to reduce the subject's opioid cravings.

In some embodiments, a method of treating a subject afflicted with a substance use disorder comprising administering to the subject the composition of the present invention comprising an effective amount of the compound so as to treat the subject afflicted with the substance use disorder.

In some embodiments, wherein the substance use disorder is opioid use disorder, alcohol use disorder or stimulant use disorder.

In some embodiments, wherein the substance use disorder is opioid use disorder, alcohol use disorder, stimulant use disorder or polydrug use disorder.

In some embodiments, wherein the stimulant use disorder is nicotine use disorder.

In some embodiments, a method of treating a subject afflicted with opioid withdrawal symptoms comprising administering to the subject the composition of the present invention comprising an effective amount of the compound so as to treat the subject afflicted with the opioid withdrawal symptoms.

In some embodiments, a method of treating a subject afflicted with opioid use disorder comprising administering to the subject an effective amount of mu-opioid receptor agonist and the composition of the present invention comprising an effective amount of the compound so as to treat the subject afflicted with the opioid use disorder.

In some embodiments, a method of treating a subject afflicted with alcohol withdrawal symptoms or stimulant withdrawal symptoms comprising administering to the subject the composition of the present invention comprising an effective amount of the compound so as to treat the subject afflicted with the opioid withdrawal symptoms.

In some embodiments, a method of treating a subject afflicted with traumatic brain injury (TBI) comprising administering to the subject the composition of the present invention comprising an effective amount of the compound so as to treat the subject afflicted with the traumatic brain injury (TBI).

In some embodiments, a method of treating a subject afflicted with Parkinson's disease comprising administering to the subject the composition of the present invention comprising an effective amount of the compound so as to treat the subject afflicted with the Parkinson's disease.

In some embodiments, a method of treating a subject afflicted with opioid use disorder comprising administering to the subject an effective amount of mu-opioid receptor agonist and the composition of the present invention comprising an effective amount of the compound so as to treat the subject afflicted with the opioid use disorder.

In some embodiments, a method of treating a subject afflicted with pain comprising administering to the subject an effective amount of an opioid or opiate and the composition of the present invention comprising an effective amount of the compound so as to treat the subject afflicted with pain.

In some embodiments, a method of treating a subject afflicted with pain comprising administering to the subject an effective amount of morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil, buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c, f][1,2]thiazepin-11-yl)amino)heptanoic acid, 7-((3-iodo-6-methyl-5,5-dioxido-6,11-dihydrodibenzo[c,f][1,2]  thiazepin-11-yl)amino)heptanoic acid, 5-((3-bromo-6-methyl-5, 5-dioxido-6,11-dihydrodibenzo[c,f][1,2]thiazepin-11-yl) amino)pentanoic acid or 5-((3-iodo-6-methyl-5,5-dioxido-6, 11-dihydrodibenzo[c,f][1,2]thiazepin-11-yl)amino) pentanoic acid and the composition of the present invention comprising an effective amount of the compound so as to treat the subject afflicted with pain.

In some embodiments, a method of treating a subject afflicted with opioid use disorder comprising administering to the subject an effective amount of an opioid or opiate and the composition of the present invention comprising an effective amount of the compound so as to treat the subject afflicted with the opioid use disorder.

In some embodiments, a method of treating a subject afflicted with opioid use disorder comprising administering to the subject an effective amount of morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil, buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c,f][1,2]thiazepin-11-yl)amino)heptanoic acid, 7-((3-iodo-6-methyl-5,5-dioxido-6,11-dihydrodibenzo [c,f][1,2]  thiazepin-11-yl)amino)heptanoic  acid, 5-((3-bromo-6-methyl-5,5-dioxido-6,11-dihydrodibenzo[c,f][1,2] thiazepin-11-yl)amino)pentanoic  acid  or  5-((3-iodo-6-methyl-5,5-dioxido-6,11-dihydrodibenzo[c,f][1,2] thiazepin-11-yl)amino)pentanoic acid and the composition of the present invention comprising an effective amount of the compound so as to treat the subject afflicted with the opioid use disorder.

In some embodiments, a method of treating a subject afflicted with opioid use disorder or opioid withdrawal symptoms comprising administering to the subject an effective amount of naloxone or methylnaltrexone and the composition of the present invention comprising an effective amount of the compound so as to thereby treat the subject afflicted with the opioid use disorder or opioid withdrawal symptoms.

The present invention also provides a compound having the structure:

or a salt thereof, for use in treating a subject afflicted with a depressive disorder, a mood disorder, an anxiety disorder, a substance use disorder, opioid withdrawal symptoms, traumatic brain injury, or Parkinson's disease.

The present invention also provides a compound having the structure:

or a salt thereof, for use in treating a subject afflicted with a depressive disorder, a mood disorder, an anxiety disorder, a substance use disorder, opioid withdrawal symptoms, traumatic brain injury, or Parkinson's disease.

The present invention further provides a pharmaceutical composition comprising an amount of a compound having the structure:

or a salt thereof, for use in treating a subject afflicted with a depressive disorder, a mood disorder, an anxiety disorder, a substance use disorder, opioid withdrawal symptoms, traumatic brain injury, or Parkinson's disease.

The present invention also provides a compound having the structure:

or a salt thereof, for use as an add-on therapy or in combination with an opioid or opiate in treating a subject afflicted with pain, a depressive disorder, a mood disorder, an anxiety disorder, a substance use disorder, opioid withdrawal symptoms, traumatic brain injury, or Parkinson's disease.

In some embodiments, a package comprising:

a) a first pharmaceutical composition comprising an amount of an opioid or opiate and a pharmaceutically acceptable carrier;

b) a second pharmaceutical composition comprising the compound of the present invention and a pharmaceutically acceptable carrier; and c) instructions for use of the first and second pharmaceutical compositions together to treat a subject afflicted with pain, a depressive disorder, a mood disorder, an anxiety disorder, a substance use disorder, opioid withdrawal symptoms, traumatic brain injury, or Parkinson's disease.

In some embodiments, a therapeutic package for dispensing to, or for use in dispensing to, a subject afflicted pain, a depressive disorder, a mood disorder, an anxiety disorder, a substance use disorder, opioid withdrawal symptoms, traumatic brain injury or Parkinson's disease, which comprises:

a) one or more unit doses, each such unit dose comprising:

(i) a pharmaceutical composition comprising the compound of the present invention; and (ii) an amount of an opioid or opiate, wherein the respective amounts of said composition and said opioid or opiate in said unit dose are effective, upon concomitant administration to said subject, to treat the subject, and (b) a finished pharmaceutical container therefor, said container containing said unit dose or unit doses, said container further containing or comprising labeling directing the use of said package in the treatment of said subject.

The therapeutic package of the above embodiment, wherein the respective amounts of said composition and opioid or opiate in said unit dose when taken together is more effective to treat the subject than when compared to the administration of said composition in the absence of said opioid or opiate or the administration of said opioid or opiate in the absence of said composition.

A pharmaceutical composition in unit dosage form, useful in treating a subject afflicted with pain, a depressive disorder, a mood disorder, an anxiety disorder, a substance use disorder, opioid withdrawal symptoms, traumatic brain injury or Parkinson's disease, which comprises:

(i) a composition comprising the compound of the present invention; and (ii) an amount of an opioid or opiate, wherein the respective amounts of said composition and said opioid or opiate in said composition are effective, upon concomitant administration to said subject of one or more of said unit dosage forms of said composition, to treat the subject.

The pharmaceutical composition of the above embodiment, wherein the respective amounts of said compound and said opioid or opiate in said unit dose when taken together is more effective to treat the subject than when compared to the administration of said composition in the absence of said opioid or opiate or the administration of said opioid or opiate in the absence of said composition.

In some embodiments of the present method, package, use or pharmaceutical composition, the compound has the structure:

In some embodiments, a pharmaceutically acceptable salt of any of the above compounds of the present invention.

In some embodiments, a salt of the compound of the present invention is used in any of the above methods, uses, packages or compositions.

In some embodiments, a pharmaceutically acceptable salt of the compound of the present invention is used in any of the above methods, uses, packages or compositions.

Any of the above compounds may be used in any of the disclosed methods, uses, packages or pharmaceutical compositions.

Any of the compounds used in the disclosed methods, uses, packages or pharmaceutical compositions may be replaced with any other compound disclosed in the present invention.

Any of the above generic compounds may be used in any of the disclosed methods, uses, packages or compositions.

In some embodiments of any of the above methods, wherein the composition is orally administered to the subject.

In some embodiments of any of the above methods, wherein 10-30 mg of the compound is administered to the subject.

In some embodiments of any of the above methods, wherein 30-100 mg of the compound is administered to the subject.

In some embodiments of any of the above methods, wherein 100-300 mg of the compound is administered to the subject.

In some embodiments of any of the above methods, wherein 300-500 mg of the compound is administered to the subject.

In some embodiments of any of the above methods, wherein 500-800 mg of the compound is administered to the subject.

In some embodiments of any of the above methods, wherein 800-1100 mg of the compound is administered to the subject.

In some embodiments of any of the above methods, wherein 1200-1500 mg of the compound is administered to the subject.

In some embodiments, a method wherein any of the above recited doses of the compound, and an opioid are administered to a subject afflicted with the substance use disorder, opioid withdrawal symptoms, pain, a mood disorder, an anxiety disorder or opioid cravings so as to thereby treat the subject afflicted with the substance use disorder, opioid withdrawal symptoms, pain or the mood disorder or reduce opioid cravings in the subject.

In some embodiments of any of the above methods, wherein the opioid is morphine and 10-20 mg (oral) or 3-5 mg (parenteral) of the opioid is administered to the subject.

In some embodiments of any of the above methods, wherein the opioid is codeine and 30-60 mg (oral) of the opioid is administered to the subject.

In some embodiments of any of the above methods, wherein the opioid is oxycodone and 5-10 mg (oral) of the opioid is administered to the subject.

In some embodiments of any of the above methods, wherein the opioid is fentanyl and 40-60 µg (parenteral) of the opioid is administered to the subject.

In some embodiments of any of the above methods, wherein the opioid is butorphanol and 1-3 mg (parenteral) of the opioid is administered to the subject.

In some embodiments of any of the above methods, wherein the opioid is nalbuphine and 5-15 mg (parenteral) of the opioid is administered to the subject.

In some embodiments of any of the above methods, wherein the opioid is nalbuphine and 5-15 mg (parenteral) of the opioid is administered to the subject.

In some embodiments of any of the above methods, wherein mitragynine (15-100 mg—oral) or 3-deuteromi-tragynine (15-100 mg—oral) is administered to the subject.

In some embodiments of any of the above methods, wherein tianeptine (12.5-100 mg—oral) is administered to the subject.

In some embodiments of any of the above methods, wherein 7-((3-iodo-6-methyl-5,5-dioxido-6,11-dihydrod-ibenzo[c,f][1,2] thiazepin-11-yl)amino)heptanoic acid (1.5-10 mg—oral) is administered to the subject.

In some embodiments of any of the above methods, wherein 5-((3-iodo-6-methyl-5,5-dioxido-6,11-dihydrod-ibenzo[c,f][1,2]thiazepin-11-yl)amino)pentanoic acid (2-20 mg—oral) is administered to the subject.

In some embodiments of any of the above methods, wherein administration of the composition of the present invention comprising an effective amount of the compound lowers the effective amount of the opioid.

In some embodiments of any of the above methods, wherein administration of the composition of the present invention lowers the effective dosage amount of the opioid by 75% or more.

In some embodiments of the above method, wherein administration of the composition of the present invention lowers the effective dosage amount of the opioid by 50% or more.

In some embodiments of the above method, wherein administration of the composition of the present invention lowers the effective dosage amount of the opioid by 25% or more.

In some embodiments of any of the above methods, wherein 0.4 mg/kg-30 mg/kg of the compound of the present invention is administered to the subject.

In some embodiments of any of the above methods, wherein 0.3-1.5 mg/kg of the opioid or opiate is administered to the subject.

In some embodiments of any of the above methods, wherein the subject is a human.

In some embodiments of any of the above methods, the composition is clinic administered or physician administered to the subject.

In some embodiments of any of the above methods, the composition is clinic self-administered by the subject.

In some embodiments of any of the above methods, wherein formation of the noribogaine is attenuated within the subject.

In some embodiments of any of the above methods, wherein formation of the noribogaine is reduced within the subject.

In some embodiments of any of the above methods, wherein duration of ibogaine is attenuated within the subject.

In some embodiments, the method wherein the subject is afflicted with a depressive disorder, a mood disorder, or an anxiety disorder.

In some embodiments, the anxiety disorder includes, but is not limited to, anxiety, generalized anxiety disorder (GAD), panic disorder, social phobia, social anxiety disorder, acute stress disorder, obsessive-compulsive disorder (OCD), or post-traumatic stress disorder (PTSD).

In some embodiments, the depressive disorder includes, but is not limited to, depression, major depression, dysthymia, cyclothymia, postpartum depression, seasonal affective disorder, atypical depression, psychotic depression, bipolar disorder, premenstrual dysphoric disorder, situational depression or adjustment disorder with depressed mood. Depressive disorders can also include other mood disorders and is not limited to the above list.

Preclinical evidence (rodents) also shows that ibogaine/noribogaine enhances morphine's analgesic effect (Sharma, S. S. et al. 1998) or reverses analgesic tolerance to morphine (Bhargava, H. N. et al. 1997).

In some embodiments, the method wherein the subject is afflicted with pain. Reports of stimulant effects of *Tabernanthe iboga* date back to late 1890's and early 1900's in the descriptions of ritual and medicinal use by the native inhabitants in Africa. Ibogaine was recommended in France to treat "asthenia" (dose range of 10-30 mg per day). In the period of 1939-1970, ibogaine was commercially available in France as "Lambaréne", a "neuromuscular stimulant" (8 mg pills) recommended for fatigue, depression, and recovery from infectious diseases (K. Alper 2001). In one clinical study, subjects took visual analog scale tests (VAS, 0-100) related to sleepiness, energetic feelings, and the side effects such as nausea, anxiety versus calmness. Subjects reported that ibogaine decreased sleepiness and increased energetic feeling over the examined 24-hour period after one dose of 20 mg of ibogaine (Glue, P. et al. 2015). A stimulant effect was reported in cats (Schneider et. al 1957). In rats, ibogaine induced wakefulness and suppressed the REM sleep as shown via EEG (Gonzalez, J. et al 2018).

It has been shown in rats that ibogaine leads to a dramatic upregulation of BDNF (in addition to GDNF) which provides structural and functional restorative effects in subjects afflicted with TBI (Marton, S. et al. 2019). The efficacy of ibogaine has also been shown in cases of soldiers afflicted with TBI and PTSD (Thoricatha, W. 2020).

In some embodiments, the method wherein the subject is afflicted with traumatic brain injury (TBI).

It has been shown in rats that ibogaine induces expression of GDNF (He, D-Y. et al. 2005 and Marton, S. et al. 2019), a critical neurotrophic factor that maintains and restores the dopaminergic system (which degenerates in Parkinson's disease). Thus, ibogaine provides structural and functional restorative effects in subjects afflicted with Parkinson's disease. GDNF itself has been shown to exert desired effects in Parkinson's rodent and monkey models (Gash, D. M. et al. 1996).

In some embodiments, the method wherein the subject is afflicted with Parkinson's disease.

It has been shown in humans that ibogaine is useful in treating opioid and stimulant use disorders (Alper, K. R. et al. 1999; Mash, D. C. et al. 2018; Schenberg, E. E. et al. 2014) or in maintenance therapy (opioid use disorder) in combination with an opioid to lower effective opioid doses (Kroupa, P. K. & Wells, H. 2005).

In some embodiments, wherein the substance use disorder is an opioid use disorder, alcohol use disorder or stimulant use disorder.

Opioid use disorder (OUD) involves, but is not limited to, misuse of opioid medications or use of illicitly obtained opioids. The Diagnostic and Statistical Manual of Mental Disorders, 5th Edition (American Psychiatric Association: Diagnostic and Statistical Manual of Mental Disorders: Diagnostic and Statistical Manual of Mental Disorders, Fifth Edition. Arlington, Va.: American Psychiatric Association, 2013), which is hereby incorporated by reference, describes opioid use disorder as a problematic pattern of opioid use leading to problems or distress, with at least two of the following occurring within a 12-month period:

Taking larger amounts or taking drugs over a longer period than in ended.

Persistent desire or unsuccessful efforts to cut down or control opioid use.

Spending a great deal of rime obtaining or using the opioid or recovering from its effects.

Craving, or a strong desire or urge to use opioids

Problems fulfilling obligations at work, school or home.

Continued opioid use despite having recurring social or interpersonal problems.

Giving up or reducing activities because of opioid use.

Using opioids in physically hazardous situations.

Continued opioid use despite ongoing physical or psychological problem likely to have been caused or worsened by opioids.

Tolerance (i.e., need for increased amounts or diminished effect with continued use of the same amount)

Experiencing withdrawal (opioid withdrawal syndrome) or taking opioids (or a closely related substance) to relieve or avoid withdrawal symptoms.

Alcohol use disorder (AUD) involves, but is not limited to, a chronic relapsing brain disease characterized by compulsive alcohol use, loss of control over alcohol intake, and a negative emotional state when not using. The Diagnostic and Statistical Manual of Mental Disorders, 5th Edition describes alcohol use disorder as a problematic pattern of alcohol use leading to problems or distress, with at least two of the following occurring within a 12-month period:

Being unable to limit the amount of alcohol you drink.

Wanting to cut down on how much you drink or making unsuccessful attempts to do so.

Spending a lot of time drinking, getting alcohol or recovering from alcohol use.

Feeling a strong craving or urge to drink alcohol.

Failing to fulfill major obligations at work, school or home due to repeated alcohol use.

Continuing to drink alcohol even though you know it's causing physical, social or interpersonal problems.

Giving up or reducing social and work activities and hobbies.

Using alcohol in situations where it's not safe, such as when driving or swimming.

Developing a tolerance to alcohol so you need more to feel its effect or you have a reduced effect from the same amount.

Experiencing withdrawal symptoms—such as nausea, sweating and shaking—when you don't drink, or drinking to avoid these symptoms Stimulant use disorder involves, but is not limited to, a pattern of problematic use of amphetamine, methamphetamine, cocaine, or other stimulants except caffeine or nicotine, leading to at least two of the following problems within a 12-month period:

Taking more stimulants than intended.

Unsuccessful in trying to cut down or control use of stimulants, despite wanting to do so.

Spending excessive amounts of time to activities surrounding stimulant use.

Urges and cravings for stimulants.

Failing in the obligations of home, school or work.

Carrying on taking stimulants, even though it has led to relationship or social problems.

Giving up or reducing important recreational, social, or work-related activities because of using stimulants.

Using stimulants in a physically hazardous way.

Continuing to use stimulants even while knowing that it is causing or worsening a physical or psychological problem.

Tolerance to stimulants.

Withdrawal from stimulants if you don't take them.

Polydrug use disorder or polysubstance use disorder involves, but is not limited to, dependence on multiple drugs or substances.

The term "MOR agonist" is intended to mean any compound or substance that activates the mu-opioid receptor (MOR). The agonist may be a partial, full or super agonist.

A person skilled in the art may use the techniques disclosed herein to prepare deuterium analogs thereof.

Except where otherwise specified, the structure of a compound of this invention includes an asymmetric carbon atom, it is understood that the compound occurs as a racemate, racemic mixture, scalemic mixtures and isolated single enantiomers. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, N Y, 1981. For example, the resolution may be carried out by preparative chromatography on a chiral column.

Except where otherwise specified, the subject invention is intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notations of a carbon in structures throughout this application, when used without further notation, are intended to represent all isotopes of carbon, such as $^{12}C$, $^{13}C$, or $^{14}C$. Furthermore, any compounds containing $^{13}C$ or $^{14}C$ may specifically have the structure of any of the compounds disclosed herein.

It will also be noted that any notations of a hydrogen (H) in structures throughout this application, when used without further notation, are intended to represent all isotopes of hydrogen, such as $^{1}H$, $^{2}H$ (D), or $^{3}H$ (T) except where otherwise specified. Furthermore, any compounds containing $^{2}H$ or $^{3}H$ may specifically have the structure of any of the compounds disclosed herein except where otherwise specified.

Isotopically-labeled compounds can generally be prepared by conventional techniques known to those skilled in the art using appropriate isotopically-labeled reagents in place of the non-labeled reagents employed.

Deuterium ($^{2}H$ or D) is a stable, non-radioactive isotope of hydrogen and has an atomic weight of 2.0144. Hydrogen atom in a compound naturally occurs as a mixture of the isotopes $^{1}H$ (hydrogen or protium), D ($^{2}H$ or deuterium), and T ($^{3}H$ or tritium). The natural abundance of deuterium is 0.0156%. Thus, in a composition comprising molecules of a naturally occurring compound, the level of deuterium at a particular hydrogen atom site in that compound is expected to be 0.0156%. Thus, a composition comprising a compound with a level of deuterium at any site of hydrogen atom in the compound that has been enriched to be greater than its natural abundance of 0.0156% is novel over its naturally occurring counterpart.

As used herein, a hydrogen at a specific site in a compound is "deuterium-enriched" if the amount of deuterium at the specific site in the compound is more than the abundance of deuterium naturally occurring at that specific site in view of all of the molecules of the compound in a defined universe such as a composition or sample. Naturally occurring as used above refers to the abundance of deuterium which would be present at a relevant site in a compound if the compound was prepared without any affirmative step to enrich the abundance of deuterium. Thus, at a "deuterium-enriched" site in a compound, the abundance of deuterium at that site can range from more than 0.0156% to 100%. Examples of ways to obtain a deuterium-enriched site in a compound are exchanging hydrogen with deuterium or synthesizing the compound with deuterium-enriched starting materials.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. An embodiment can be $C_1$-$C_8$ alkyl, $C_2$-$C_8$ alkyl, $C_3$-$C_8$ alkyl, $C_4$-$C_8$ alkyl and so on. "Alkoxy" represents an alkyl group as described above attached through an oxygen bridge.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Another aspect of the invention comprises a compound or composition of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department of Health and Human Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat a disease or medical disorder, the salt is pharmaceutically acceptable. Examples of pharmaceutically acceptable salts include, but are not limited to, mineral or organic acid salts of basic residues such as amines; alkali or organic salts of acidic residues such as phenols; alkali or organic salts of acidic residues such as carboxylic acids. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the sodium, potassium, or lithium salts, and the like. Carboxylate salts are the sodium, potassium, or lithium salts, and the like. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease. Treating may also mean improving one or more symptoms of a disease.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier, as are capsules, coatings and various syringes.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of disease, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al. 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, 17th ed., 1989, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

Each embodiment disclosed herein is contemplated as being applicable to each of the other disclosed embodiments. Thus, all combinations of the various elements described herein are within the scope of the invention. Any of the disclosed generic or specific compounds may be applicable to any of the disclosed compositions, processes or methods.

This invention will be better understood by reference to the Experimental Details which follow, but those skilled in the art will readily appreciate that the specific experiments detailed are only illustrative of the invention as described more fully in the claims, which follow thereafter.

Experimental Details

General Considerations. Reagents and solvents were obtained from commercial sources and were used without further purification unless otherwise stated. Reactions were monitored by TLC using solvent mixtures appropriate to each reaction. All column chromatography was performed on silica gel (40-63 $\mu$m). Preparative TLC was conducted on glass plates coated with a 1 mm silica layer. Nuclear magnetic resonance spectra were recorded on Bruker 400 or 500 MHz instruments, as indicated. Chemical shifts are reported as $\delta$ values in ppm referenced to $CDCl_3$ ($^1H$ NMR=7.26 and $^{13}C$ NMR=77.16) or methanol-d$_4$ ($^1H$ NMR=3.31 and $^{13}C$ NMR=49.00). Multiplicity is indicated as follows: s (singlet); d (doublet); t (triplet); q (quartet); dd (doublet of doublets); td (triplet of doublets); dt (doublet of triplets); ddd (doublet of doublet of doublets); m (multiplet); br (broad). All carbon peaks are rounded to one decimal place unless such rounding would cause two close peaks to become identical; in these cases, two decimal places are retained. Low-resolution mass spectra were recorded on an Advion quadrupole instrument (ionization mode: APCI+). Percent deuteration was determined by mass spectrometry on a high-resolution quadrupole-time-of-flight instrument (ionization mode: ESI+) by quantitative comparison of the isotope pattern of deuterated compounds to controls having natural isotopic abundance.

Metabolism Studies. Metabolic stability of test compounds was evaluated in liver microsomes from rat (RLM) and human (HLM). This was accomplished by incubating test compounds with microsomes and monitoring disappearance of parent compound as well as metabolite formation over time using LC-MS/MS in Multiple Reaction Monitoring mode (MRM). Verapamil in HLM and RLM was used as positive control. Pooled human liver microsomes or pooled male rats liver microsomes (20 mg/mL) were diluted in Kphos buffer to prepare a concentration of 0.714 mg/mL.

Preparation of Test Compounds

Stock solutions of test compounds were prepared in DMSO at a concentration of 10 mM.

Assay Conditions

Total Incubation volume: 100 $\mu$L

Compound concentration: 10 $\mu$M

Protein Concentration: 0.5 mg/mL (0.25 mg/mL for positive controls)

NADPH: 1 mM

Final DMSO content: 0.1%

Number of replicates: 2

Time points: 0, 5, 15, 30 and 60 min

Assay

An 1120 $\mu$L aliquot of Kphos buffer (50 mM, pH 7.4) containing liver microsomes (0.714 mg/mL) were added to individual 2 mL tubes (final concentration 0.5 mg/mL). Test compounds (10 mM) and positive control were directly spiked into respective tubes to prepare a concentration of 14.28 $\mu$M (final concentration 10 $\mu$M). From the above mix, 70 PL was added to individual wells of 96 well reaction plates and pre-incubated at 37° C. for 5 min. All the reactions were initiated by adding 30 μL of 3.33 mM NADPH (final concentration 1 mM). Reactions without NADPH and buffer controls (minus NADPH) at 0 min and 60 min were also incubated to rule out non-NADPH metabolism or chemical instability in the incubation buffer. All reactions were terminated using 100 μL of ice-cold acetonitrile containing internal standard (glipizide) at 0, 5, 15, 30 and 60 min. The plates were centrifuged at 4000 RPM for 15 min and 100 μL aliquots were submitted for analysis by LC-MS/MS.

Preparation of Calibration Curve

Stock solution of noribogaine was prepared in DMSO at a concentration of 20 mM and serially diluted in DMSO to prepare 10, 3, 1, 0.3, 0.1 and 0.03 mM solutions respectively. These were diluted 1000 folds in microsomes to attain final concentration of 20, 10, 3, 1, 0.3, 0.1 and 0.03 μM respectively.

Bio-Analysis

Samples were monitored for parent compounds disappearance and formation of metabolite in MRM mode using LC-MS/MS instrument (API-4000 with Waters UPLC).

LC-MS/MS Conditions

| Mobile Phase | A: 0.1% Formic acid in Acetonitrile |
| | B: 10 mM Ammonium formate in water |
| Column | Accucore C8, 50 × 2.1 mm, 2.6 μm |
| Injection Volume (μL) | 1 |
| Column Oven Temperature (° C.) | 45 |

LC Gradient Used

| Time (min) | Flow (mL/min) | PUMP A (% Conc.) | PUMP B (% Conc.) |
| --- | --- | --- | --- |
| Initial | 0.6 | 0 | 100 |
| 0.3 | 0.6 | 0 | 100 |
| 0.5 | 0.6 | 95 | 5 |
| 1.4 | 0.6 | 95 | 5 |
| 1.8 | 0.6 | 0 | 100 |
| 2.2 | 0.6 | 0 | 100 |

Retention Times and MRM Transitions in Positive Polarity Mode

| Analyte ID/IS ID | Retention time (min) | Q1 | Q3 | DP | CE | CXP | Dwell time (msec) |
| --- | --- | --- | --- | --- | --- | --- | --- |
| Noribogaine | 1.05 | 297.7 | 160 | 114 | 45 | 11 | 10 |
| Ibogaine | 1.08 | 311.9 | 122.2 | 72 | 46 | 22 | |
| CD$_3$O-Ibogamine | 1.08 | 314.1 | 122.2 | 111 | 47 | 23 | |
| EtO-Ibogamine | 1.10 | 325.1 | 188.2 | 100 | 42 | 14 | |
| Glipizide | 1.05 | 446.3 | 347.0 | 40 | 22 | 12 | |
| Verapamil | 0.94 | 455.5 | 165.5 | 105 | 42 | 11 | |

Source Parameters

| Source Parameter | Parameter value/ description |
| --- | --- |
| Polarity | Positive |
| CAD | 8 |
| CUR | 30 |
| GS1 | 40 |
| GS2 | 60 |
| Ion Spray Voltage | 5500 |
| Temperature | 550 |

-continued

| Source Parameter | Parameter value/ description |
| --- | --- |
| Interface Heater | ON |
| EP | 10 |

Data Analysis

The percent remaining of test compounds and positive control in each sample was determined by considering peak area ratio in the 0 minute sample as 100%. The Half-life of compounds in microsomes is calculated by formula:

Half-life ($t_{1/2}$) (min)=0.693/$k$, where $k$ is gradient of line determined from plot of peak area ratio (compound peak area/internal standard peak area) against time.

In vitro intrinsic clearance (CL'int) (units in mL/min/kg) was calculated using the formula:

$$CL'_{int} = \frac{0.693}{in\ vitro\ T1/2} \cdot \frac{mL\ incubation}{mg\ microsomes} \cdot \frac{45\ mg\ microsomes}{gm\ liver} \cdot \frac{liver\ weight\ in\ gm^*}{Kg\ b.w}$$

For liver microsomes, scaling factor used was 45 mg microsomal protein per gm liver.

\* Indicates liver weight (gm) which varies species wise. For human, monkey, dog, rat and mouse the liver weight are 20 gm, 32 gm, 32 gm, 40 gm and 90 gm respectively.

Example 1. Synthesis of Deuterated Ibogaine Analogs

Voacangine (184 mg, 0.5 mmol) was dissolved in CH$_2$Cl$_2$ (anhydrous, 0.75 mL), the solution was cooled in ice bath and treated with EtSH (162 μL, 2.3 mmol) followed by BBr$_3$ (1M in CH$_2$Cl$_2$, 0.75 mL). Reaction mixture was allowed to warm to room temperature and stirred for 1 h. Reaction was quenched by addition of CH$_2$Cl$_2$/iPrOH (9:1, 5 mL), the resulting solution was poured into sat. NaHCO$_3$ solution (15 mL) and extracted with CH$_2$Cl$_2$ (3×5 mL). Combined extracts were dried over Na$_2$SO$_4$, concentrated under reduce pressure and the crude material was filtered through a plug of silica gel in AcOEt:Hex (1:1) to obtain the product as an off-white amorphous solid (175 mg, 99%).

$^1$H NMR (500 MHz, CDCl$_3$) δ 7.65 (s, 1H), 7.09 (d, J=8.6 Hz, 1H), 6.88 (d, J=2.5 Hz, 1H), 6.71 (dd, J=8.4, 2.4 Hz,

1H), 4.61 (s, 1H), 3.72 (s, 3H), 3.54 (s, 1H), 3.42-3.32 (m, 1H), 3.24-3.15 (m, 1H), 3.15-3.05 (m, 1H), 2.96-2.87 (m, 2H), 2.83-2.78 (m, 1H), 2.58 (dt, J=15.2, 3.1 Hz, 1H), 1.93-1.85 (m, 2H), 1.77-1.69 (m, 1H), 1.63-1.52 (m, 1H), 1.50-1.38 (m, 1H), 1.36-1.28 (m, 1H), 1.17-1.09 (m, 1H), 0.90 (t, J=7.4 Hz, 3H). $^{13}$C NMR (126 MHz, CDCl$_3$) $\delta$ 175.9, 149.4, 138.0, 130.8, 129.8, 111.5, 111.1, 110.0, 103.4, 57.7, 55.3, 53.2, 52.8, 51.6, 39.3, 36.7, 32.2, 27.5, 26.9, 22.3, 11.8. LRMS (APCI+) calcd. for C$_{21}$H$_{27}$N$_2$O$_3$$^+$ [M+H]$^+$ 355.2, found 355.1.

10-hydroxycorronaridine (106 mg, 0.3 mmol) and K$_2$CO$_3$ (97 mg, 0.7 mmol) were combined in DMF (anhydrous, 1.2 mL) and CD$_3$I (37 μL, 0.6 mmol) was added. Reaction mixture was further stirred 20 h under argon atmosphere and quenched by pouring into H$_2$O (15 mL). Aqueous mixture was extracted with Et$_2$O (3×5 mL), combined extracts were washed with H$_2$O (10 mL), brine (10 mL), dried over Na$_2$SO$_4$ and concentrated under reduce pressure. Crude material was purified by preparative TLC using AcOEt (15%) in hexanes. Product was obtained as an off-white solid (80 mg, 72%).

$^1$H NMR (500 MHz, CDCl$_3$) $\delta$ 7.68 (s, 1H), 7.14 (dd, J=8.7, 0.6 Hz, 1H), 6.93 (dt, J=2.5, 0.6 Hz, 1H), 6.81 (dd, J=8.7, 2.4 Hz, 1H), 3.71 (s, 3H), 3.56-3.54 (m, 1H), 3.42-3.36 (m, 1H), 3.25-3.12 (m, 2H), 3.00-2.89 (m, 2H), 2.82 (dt, J=8.6, 1.5 Hz, 1H), 2.61-2.55 (m, 1H), 1.92-1.86 (m, 2H), 1.77-1.70 (m, 1H), 1.62-1.54 (m, 1H), 1.49-1.40 (m, 1H), 1.37-1.29 (m, 1H), 1.16-1.10 (m, 1H), 0.90 (t, J=7.4 Hz, 3H). $^{13}$C NMR (126 MHz, CDCl$_3$) $\delta$ 175.8, 154.1, 137.7, 130.7, 129.3, 111.9, 111.2, 110.3, 100.9, 57.7, 55.3, 53.3, 52.7, 51.7, 39.3, 36.7, 32.2, 27.5, 26.9, 22.4, 11.8 ($^{13}$C signal for CD$_3$O— group was not observed, lower intensity and complex splitting due to D labeling). HRMS (ESI+) calcd. for C$_{22}$H$_{26}$D$_3$N$_2$O$_3$$^+$ [M+H]$^+$ 372.2361, found 372.2367, extent of deuteration after correction for natural deuterium content: —OCH$_3$ 0.00%; —OCH$_2$D: 0.33%; —OCH$_2$D: 0.62% and —OCD$_3$: 99.05%.

-continued

Solid KOH (135 mg, 2.4 mmol, 10 eq) was added to a solution of voacangine-d$_3$ (90 mg, 0.24 mmol) in (EtOH: H$_2$O) (3:2) (6 mL, 0.04 M) in a two neck round bottom flask. The stirred solution was flushed with argon for 15 minutes to remove dissolved oxygen. The reaction mixture was further heated to reflux for 15 h, until all starting material was consumed, as evidenced by TLC (8:2, Hex:AcOEt+1% NH$_4$OH). The solution was allowed to cool down to room temperature and HCl 5N (1.8 mL, 9.0 mmol, 37 eq) was added and the reflux was continued for another 15 minutes. The reaction mixture was allowed to cool down to room temperature and the solution was neutralized with solid NaHCO$_3$. Ethanol was evaporated under reduced pressure (until constant volume), and the aqueous phase was extract with AcOEt (3×), the combined organic extracts were dried over Na$_2$SO$_4$, and the solvent was removed under reduced pressure. The crude material was purified by column chromatography (8:2, Hexanes:AcOEt+1% NH$_4$OH). CD$_3$O-ibogamine was obtained as a white solid (60 mg, 80%).

$^1$H NMR (400 MHz, CDCl$_3$) $\delta$ 7.51 (s, 1H), 7.14 (d, J=8.6 Hz, 1H), 6.92 (d, J=2.4 Hz, 1H), 6.76 (dd, J=8.7, 2.4 Hz, 1H), 3.41-3.28 (m, 2H), 3.18-3.10 (m, 1H), 3.07 (dt, J=9.3, 2.3 Hz, 1H), 2.97 (dt, J=9.4, 3.0 Hz, 1H), 2.93-2.87 (m, 1H), 2.86-2.81 (m, 1H), 2.70-2.51 (m, 1H), 2.11-1.97 (m, 1H), 1.88-1.81 (m, 1H), 1.82-1.74 (m, 1H), 1.70-1.60 (m, 1H), 1.58-1.49 (m, 3H), 1.50-1.39 (m, 1H), 1.26-1.15 (m, 1H), 0.89 (t, J=7.1 Hz, 3H). $^{13}$C NMR (101 MHz, CDCl$_3$) $\delta$ 154.0, 142.8, 130.1, 129.7, 110.8, 110.7, 109.2, 100.4, 57.6, 54.2, 50.0, 42.0, 41.6, 34.2, 32.1, 27.8, 26.5, 20.7, 11.9 ($^{13}$C signal for CD$_3$O— group was not observed, lower intensity and complex splitting due to D labeling). GC-MS (EI, 70 eV): 313.25, 312.25, 228.10, 149.20, 136.15, 135.15. Isotopic abundance: 0.1243% of —CHD$_2$; 0.0131% of —CH$_2$D; 0.0218% of —CH$_3$ relative to —CD$_3$.

Noribogaine hydrochloride (166 mg, 0.5 mmol) and $K_2CO_3$ (276 mg, 2.0 mmol) were combined in DMF (anhydrous, 2.0 mL) and $CH_3CH_2I$ (80 µL, 1.0 mmol) was added. Reaction mixture was further stirred 23 h under argon atmosphere and quenched by pouring into $H_2O$ (20 mL). Aqueous mixture was extracted with $Et_2O$ (3×10 mL), combined extracts were washed with $H_2O$ (10 mL), brine (10 mL) and dried over $Na_2SO_4$. Crude material was purified by column chromatography ($Et_2O$ in Hexanes+2% $Et_3N$, gradient of 0%, 10%, 20 and 25 $Et_2O$). Product was obtained as a thick colorless oil (143 mg, 88%).

$^1$H NMR (500 MHz, $CDCl_3$) δ 7.55 (s, 1H), 7.13 (d, J=8.6 Hz, 1H), 6.95 (d, J=2.4 Hz, 1H), 6.78 (dd, J=8.6, 2.4 Hz, 1H), 4.09 (q, J=7.0 Hz, 2H), 3.42-3.28 (m, 2H), 3.20-3.04 (m, 2H), 2.98 (dt, J=9.4, 3.0 Hz, 1H), 2.94-2.81 (m, 2H), 2.66-2.55 (m, 1H), 2.09-1.98 (m, 1H), 1.90-1.74 (m, 2H), 1.69-1.61 (m, 1H), 1.61-1.51 (m, 2H), 1.45 (q, J=8.4, 7.0 Hz, 4H), 1.25-1.17 (m, 1H), 0.91 (t, J=7.0 Hz, 3H). $^{13}$C NMR (126 MHz, $CDCl_3$) δ 153.3, 143.0, 130.3, 129.9, 111.4, 110.9, 109.2, 101.8, 64.5, 57.6, 54.3, 50.1, 42.1, 41.7, 34.3, 32.2, 28.0, 26.6, 20.8, 15.3, 12.1. LRMS (APCI+) calcd. for $C_{21}H_{29}N_2O^+$ [M+H]$^+$ 325.2, found 325.2

Figure 1A:
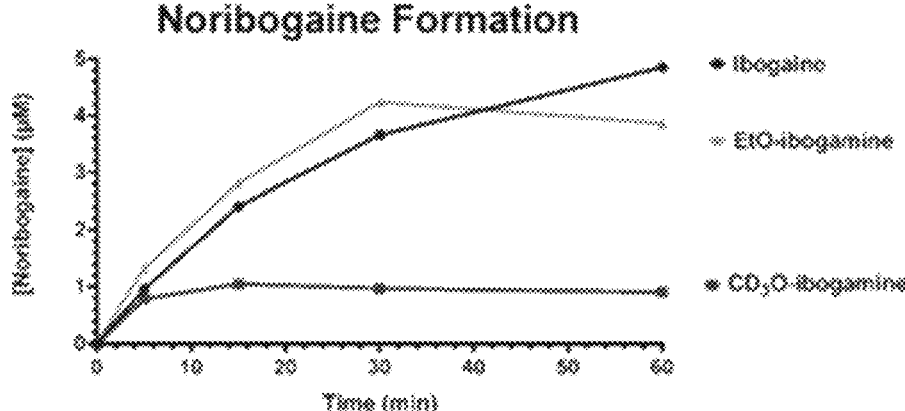
Figure 1B:
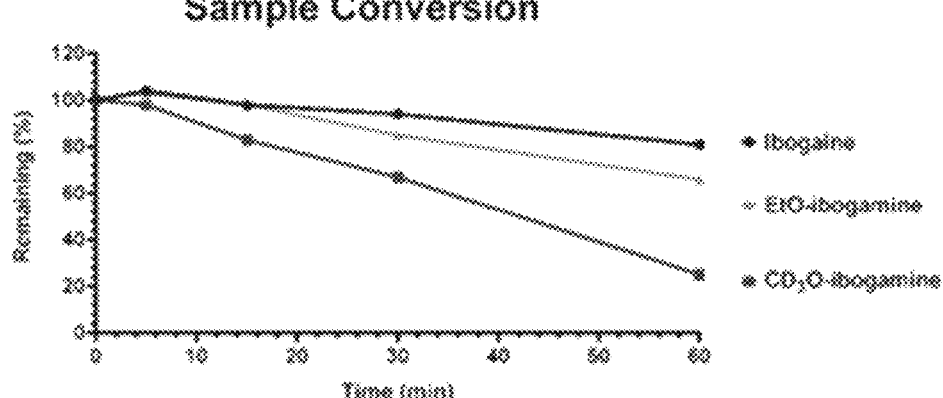
FIG. 1B: Conversion of ibogaine and its derivatives to noribogaine in human liver microsomes.
Figure 1B:
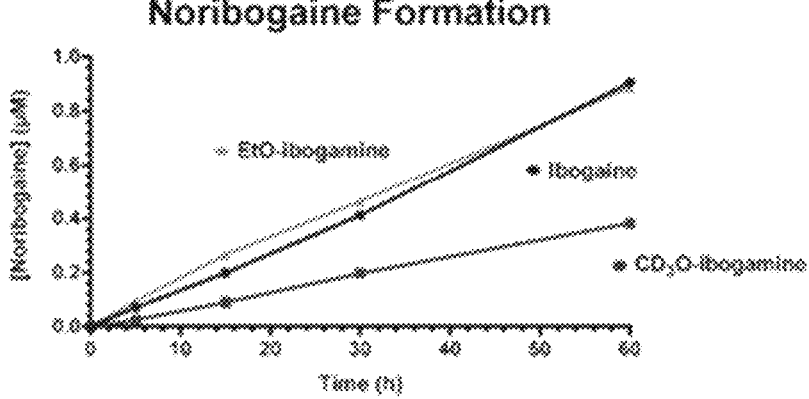

Example 2A. Metabolism of $CD_3O$-ibogamine $CD_3O$-ibogamine metabolic degradation in human liver microsomes (HLM) was more than 2× faster compared to that of ibogaine, while the formation of noribogaine was more than 2× slower compared to that of ibogaine (Scheme 1, Tables 1-2 and FIG. 1).

A similar trend was found in rat liver microsome (RLM), $t_{1/2}$/(ibo turnover)=8 min, but $t_{1/2}$/($CD_3$ turnover)<5 min rate of noribogaine formation >4× lower compared to ibogaine.

Scheme 1.

Ibogaine
(natural product)

$t_{1/2(ibo\ turnover)} > 60$ min

Slope of metabolite
formation 0.01475

-continued

Noribogaine
(formed as metabolite)

$CD_3O$-ibogamine

HLM $t_{1/2(CD3\ turnover)} = 30$ min

Slope of metabolite
formation 0.006381

Noribogaine

TABLE 1

Percentage turnover of test compounds in rat (RLM) and human liver microsomes (HLM).

| Time (min) | Verapamil | | Ibogaine | | $CD_3O$-Ibogamine | | EtO-Ibogamine | |
|---|---|---|---|---|---|---|---|---|
| | RLM | HLM | RLM | HLM | RLM | HLM | RLM | HLM |
| 0 | 100 | 100 | 100 | 100 | 100 | 100 | 100 | 100 |
| 5 | 72 | 67 | 86 | 104 | 36 | 98 | 77 | 103 |
| 15 | 51 | 49 | 56 | 98 | 0 | 83 | 42 | 98 |
| 30 | 35 | 38 | 23 | 94 | 1 | 67 | 3 | 85 |
| 60 | 20 | 21 | 1 | 81 | 0 | 25 | 0 | 66 |
| % Remaining at 60 min (+NADPH) | 20 | 21 | 1 | 81 | 0 | 25 | 0 | 66 |
| % Remaining at 60 min (−NADPH) | 98 | 104 | 104 | 98 | 105 | 105 | 88 | 106 |
| % Remaining at 60 min (Buffer) | 120 | | 103 | | 90 | | 88 | |
| $t_{1/2}$ (min) | 27 | 29 | 8 | >60 | <5 | 30 | 6 | >60 |
| $CL_{h,\ int}$ (mL/min/kg) | 185 | 85 | 306 | 7 | 742 | 42 | 445 | 13 |

TABLE 2

| | | | | | | |
|---|---|---|---|---|---|---|
| Concentrations (µM) of noribogaine detected in samples of ibogaine, CD₃O-ibogamine and EtO-ibogamine in the course of microsomal transformation. | | | | | | |
| | Ibogaine | | CD₃O-Ibogamine | | EtO-Ibogamine | |
| Time (min) | RLM | HLM | RLM | HLM | RLM | HLM |
| 0 | 0.000 | 0.000 | 0.000 | 0.000 | 0.02 | 0.000 |
| 5 | 0.960 | 0.071 | 0.785 | 0.026 | 1.320 | 0.095 |
| 15 | 2.405 | 0.198 | 1.050 | 0.090 | 2.810 | 0.266 |
| 30 | 3.660 | 0.412 | 0.970 | 0.197 | 4.240 | 0.464 |
| 60 | 4.855 | 0.906 | 0.905 | 0.382 | 3.865 | 0.886 |

Example 2B. Metabolism of Deuterated Ibogaine Analogs

A similar analysis is performed with each of $CD_2HO$-ibogamine, $CDH_2O$-ibogamine, $CD_3CD_2O$-ibogamine, $CD_3CH_2O$-ibogamine, $CH_3CD_2O$-ibogamine and $CH_3CDHO$-ibogamine. The analysis shows that degradation of each of the above listed compounds is at least as fast or faster than ibogaine, while the formation of noribogaine is as fast or slower compared to that of ibogaine.

Example 3. Administration of Deuterated Analogs

An amount of a composition comprising any one of $CD_3O$-ibogamine, $CD_2HO$-ibogamine, $CDH_2O$-ibogamine, $CD_3CD_2O$-ibogamine, $CD_3CH_2O$-ibogamine, $CH_3CD_2O$-ibogamine, or $CH_3CDHO$-ibogamine is administered to a subject afflicted with a substance use disorder. The amount of the compound in the composition is effective to treat the subject. In these structures, D represents a deuterium-enriched site.

An amount of a composition comprising any one of $CD_3O$-ibogamine, $CD_2HO$-ibogamine, $CDH_2O$-ibogamine, $CD_3CD_2O$-ibogamine, $CD_3CH_2O$-ibogamine or $CH_3CD_2O$-ibogamine is administered to a subject afflicted with opioid use disorder or opioid withdrawal symptoms. The amount of the compound in the composition is effective to treat the subject. In these structures, D represents a deuterium-enriched site.

An amount of a composition comprising any one of $CD_3O$-ibogamine, $CD_2HO$-ibogamine, $CDH_2O$-ibogamine, $CD_3CD_2O$-ibogamine, $CD_3CH_2O$-ibogamine or $CH_3CD_2O$-ibogamine is administered to a subject afflicted with a depressive disorder, a mood disorder, an anxiety disorder, a substance use disorder, opioid withdrawal symptoms, traumatic brain injury or Parkinson's disease. The amount of the compound in the composition is effective to treat the subject. In these structures, D represents a deuterium-enriched site.

The above therapeutic effects are improved relative to the non-deuterated compounds because in vivo formation of noribogaine is attenuated.

Example 4. Combinations with Mu-opioid Receptor Agonist

Pharmaceutical compositions of the compounds disclosed herein, combined with a mu-opioid receptor agonist, are useful in the treatment of substance use disorders with increased efficacy and/or slower development of tolerance. Alternatively, the composition and agonist may be dosed separately, as a novel method for treating substance use disorders.

Non-Limiting Examples of Mu-Opioid Receptor Agonists:

morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c,f][1,2]thiazepin-11-yl)amino)heptanoic acid, 7-((3-iodo-6-methyl-5,5-dioxido-6,11-dihydrodibenzo[c,f][1,2] thiazepin-11-yl) amino)heptanoic acid, 5-((3-bromo-6-methyl-5,5-dioxido-6, 11-dihydrodibenzo[c,f][1,2]thiazepin-11-yl)amino) pentanoic acid or 5-((3-iodo-6-methyl-5,5-dioxido-6,11-dihydrodibenzo[c,f][1,2]thiazepin-11-yl)amino)pentanoic acid.

Example 5. Pharmacokinetic Study of Deuterated Ibogaine Analogs in a Rat Animal Model Plasma pharmacokinetics and brain distribution of ibogaine, $CD_3O$-ibogamine and the common metabolite noribogaine were determined in two study groups (2×18 animals) of male Wistar rats following a single intraperitoneal (40 mg/kg) administration of ibogaine and $CD_3O$-ibogamine (3 animals per time point, 6 time points for each administered compound).

Sample Formulation

Solution of ibogaine/$CD_3O$-ibogamine were administered in 10% ethanol and 90% normal saline via intraperitoneal route. Formulation strengths for intraperitoneal administration was 4 mg/mL. A weighed quantity of compound was combined with an appropriate volume of vehicle (10% ethanol and 90% normal saline), the mixture was warmed to 55° C. and vortexed until a clear yellowish solution was obtained. The dosing volume administered was 10 mL/kg for intraperitoneal route.

Test Subjects

Healthy male Wistar rats (8-12 weeks old) weighing between 280 to 300 g were procured from Global, India. Three rats were housed in each cage. Temperature and humidity were maintained at 22±3° C. and 30-70%, respectively and illumination was controlled to give a sequence of 12 h light and 12 h dark cycle. Temperature and humidity were recorded by auto-controlled data logger system. All the animals were provided laboratory rodent diet (Envigo Research private Ltd, Hyderabad). Reverse osmosis water treated with ultraviolet light was provided ad libitum.

Sample Collection

Blood samples (approximately 120 µL) were collected under light isoflurane anesthesia from retro orbital plexus from a set of three rats at specified time intervals. Samples were collected into labeled micro-tubes, containing $K_2EDTA$ solution (10 µL of 20% $K_2EDTA$ of solution per mL of blood) as an anticoagulant. Plasma was immediately harvested from the blood by centrifugation at 4000 rpm for 10 min at 4±2° C. and stored below −70±10° C. until bioanalysis.

Immediately, after blood collection animals were euthanized with excess $CO_2$ and brain was isolated at each time point. Brain was rinsed three times in ice cold PBS (for 5-10 seconds/rinse using ~5-10 mL fresh PBS in disposable petri dish for each rinse) and dried on blotting paper. Brain samples were homogenized using ice-cold phosphate buffer saline (pH 7.4) and homogenates were stored below −70±10° C. until analysis. Total homogenate volume was three times the tissue weight.

Bioanalysis

Concentrations of nor/ibogaine/CD$_3$O-ibogamine in rat plasma and brain samples were determined by fit-for-purpose LC-MS/MS method usingWaters® UPLC-MS\MS-API 4000 equipped with either Triple Quadra or Q-TRAP mass spectrometer (AB Sciex).

Mobile Phase A: 0.1% Formic acid in Acetonitrile B: 10 mM Ammonium Formate

Column: Waters Phenyl, 50×2.1 mm, 2.7 µm

Injection Volume: 2 µL

Column Oven Temperature: 45° C.

LC Gradient Used for Ibogaine/CD$_3$O-Ibogamine

| Time (min) | Flow Rate (mL/min) | PUMP A (%) | PUMP B (%) |
|---|---|---|---|
| Initial | 0.6 | 0 | 100 |
| 0.3 | | 0 | 100 |
| 0.5 | | 95 | 5 |
| 1.4 | | 95 | 5 |
| 1.6 | | 0 | 100 |
| 2.0 | | 0 | 100 |

Mass Conditions
MRM Transitions:

| Analyte/IS ID | Q1 | Q3 | DP | CE | CXP | Dwell time (msec) |
|---|---|---|---|---|---|---|
| Ibogaine | 311.9 | 122.2 | 72 | 46 | 22 | 50 |
| CD$_3$O-ibogamine | 314.1 | 122.2 | 111 | 47 | 23 | 50 |
| Glipizide | 446.3 | 370.0 | 40 | 22 | 12 | 50 |

IS: Internal Standard

Source Parameter:

| Polarity | Positive |
|---|---|
| CAD | 8 |
| CUR | 25 |
| GS1 | 40 |
| GS2 | 60 |
| Ion Spray Voltage | 5500 |
| Temperature | 550 |
| Interface Heater | ON |
| EP | 10 |

The extraction procedure for plasma and brain samples and the spiked plasma and brain calibration standards were identical: A 25 PL of study sample or spiked plasma and brain calibration standard was added to individual pre-labeled micro-centrifuge tubes followed by 100 PL of internal standard prepared in Acetonitrile (Glipizide, 500 ng/mL) was added except for blank, where 100 µL of Acetonitrile was added. Samples were vortexed for 5 minutes and then centrifuged for 10 minutes at a speed of 4000 rpm at 4° C. Following centrifugation, 100 µL of clear supernatant was transferred to a 96 well plate and analyzed using LC-MS/MS.

Data Analysis

Non-compartmental analysis tool of Phoenix WinNonlin® (Version 7.0) was used to assess the pharmacokinetic parameters. Peak plasma concentrations (Cmax) and time for the peak plasma concentrations (Tmax) were the observed values. The areas under the concentration time curve (AUC$_{last}$ and AUC$_{inf}$) were calculated by linear trapezoidal rule. The terminal elimination rate constant, ke was determined by regression analysis of the linear terminal portion of the log plasma concentration-time curve. The terminal half-life (T$_{1/2}$) was estimated by 0.693/ke; CL$_{i.v.}$=Dose/AUC$_{inf}$; V$_{ss}$=MRT X CL$_{i.v.}$; % F=[(Mean AUC$_{p.o.}$×Dose$_{i.v.}$)/(Mean AUC$_{i.v.}$×Dose$_{p.o.}$)]×100

Determined Pharmacokinetic Parameters

TABLE 3

Pharmacokinetics data of ibogaine and noribogaine in male Wistar rats following a single intraperitoneal administration of ibogaine (Dose: 40 mg/kg).

| Analyte | Matrix | Tmax (h) | Cmax (ng/mL) | AUClast (h * ng/mL) |
|---|---|---|---|---|
| Ibogaine | Plasma | 0.08 | 1545.13 | 2138.81 |
| Noribogaine | | 1.00 | 1455.48 | 3031.79 |

| Analyte | Matrix | Tmax (h) | Cmax (ng/g) | AUClast (h * ng/g) | Brain-Kp (Cmax) | Brain-Kp (AUClast) |
|---|---|---|---|---|---|---|
| Ibogaine | Brain | 0.25 | 25902.26 | 24577.92 | 16.76 | 11.49 |
| Noribogaine | | 1.00 | 17727.39 | 39658.47 | 12.18 | 13.08 |

TABLE 4

Pharmacokinetics data of CD$_3$O-ibogamine and noribogaine in male Wistar rats following a single intraperitoneal administration of CD$_3$O-ibogamine (Dose: 40 mg/kg).

| Analyte | Matrix | Tmax (h) | Cmax (ng/mL) | AUClast (h * ng/mL) |
|---|---|---|---|---|
| CD$_3$O-ibogamine | Plasma | 0.08 | 1229.19 | 1698.92 |
| Noribogaine | | 1.00 | 736.02 | 1966.57 |

TABLE 4-continued

Pharmacokinetics data of $CD_3O$-ibogamine and noribogaine
in male Wistar rats following a single intraperitoneal administration
of $CD_3O$-ibogamine (Dose: 40 mg/kg).

| Analyte | Matrix | Tmax (h) | Cmax (ng/g) | AUClast (h * ng/g) | Brain-Kp (Cmax) | Brain-Kp (AUClast) |
|---|---|---|---|---|---|---|
| $CD_3O$-ibogamine | Brain | 0.08 | 11340.34 | 16357.31 | 9.23 | 9.62 |
| Noribogaine | | 2.00 | 14939.68 | 36953.27 | 20.30 | 18.79 |

TABLE 5

Mean plasma (ng/mL) and brain concentrations (ng/g) of ibogaine
and noribogaine in male Wistar rats following a single intraperitoneal
administration of ibogaine (Dose: 40 mg/kg).

| Analyte | Matrix | Time (h) 0.08 | 0.25 | 0.5 | 1 | 2 | 3 |
|---|---|---|---|---|---|---|---|
| Ibogaine | Plasma | 1545 | 1269 | 987 | 769 | 530 | 404 |
| | Brain | 24369 | 25902 | 10946 | 7013 | 4778 | 3899 |
| Noribogaine | Plasma | 312 | 871 | 1179 | 1455 | 846 | 861 |
| | Brain | 2383 | 17341 | 14563 | 17727 | 11692 | 10540 |

TABLE 6

Mean plasma (ng/mL) and brain concentrations (ng/g) of $CD_3O$-ibogamine
and noribogaine in male Wistar rats following a single intraperitoneal
administration of $CD_3O$-ibogamine (Dose: 40 mg/kg).

| Analyte | Matrix | Time (h) 0.08 | 0.25 | 0.5 | 1 | 2 | 3 |
|---|---|---|---|---|---|---|---|
| $CD_3O$-ibogamine | Plasma | 1229 | 1135 | 698 | 620 | 343 | 473 |
| | Brain | 11340 | 10199 | 6647 | 5363 | 3941 | 4684 |
| Noribogaine | Plasma | 208 | 728 | 677 | 736 | 690 | 584 |
| | Brain | 2997 | 12089 | 10413 | 13254 | 14940 | 10509 |

Protein unbound fraction (free concentration) of ibogaine (CD₃O-ibogamine) and noribogaine was estimated using the published plasma protein and rat brain tissue binding values (Rodriguez, P. et al. 2020).

DISCUSSION

Noribogaine presents cardiac safety issues owing to hERG inhibition in vitro (Rubi, L. et al. 2017) and QTc prolongation effects in humans in vivo (Glue, P. et al. 2016). These effects are compounded by the long exposure to noribogaine in vivo after the ibogaine administration of therapeutic doses. Noribogaine supersedes ibogaine as the main circulating species (several hours in humans after oral administration, >30 min in rats after i.p. administration) (Mash, D. C. et al. 1998) and exhibits slow clearance, resulting in a long exposure to this metabolite, which in turn increases the risk of adverse effects. In this invention we demonstrate that deuteration of the ibogaine's methoxy group results in highly unexpected effects, namely faster metabolic turnover of ibogaine and slower formation of noribogaine. This provides new means for tuning exposure to ibogaine and noribogaine, controlling the duration of ibogaine's psychedelic effects and mitigating cardiac adverse effects.

$CD_3O$-ibogamine metabolic degradation in human liver microsomes (HML) is more than 2× faster compared to that of ibogaine, while the formation of noribogaine is more than 2× slower. This is a highly surprising result. A person of skill in the art would have expected the opposite in term of the ibogaine metabolism: slower metabolic degradation of ibogaine, and correspondingly slower formation of noribogaine, or no change relative to ibogaine and noribogaine.

The highly unexpected nature of these findings is further supported by showing that the ethyl substituent in the 10-ethoxy-ibogamine (Scheme 2) is removed at rates of conversion of this compound and formation of noribogaine essentially the same to those of ibogaine.

Scheme 2.

$CH_3CH_2O$ — 10-ethoxy ibogamine

HLM
human liver microsomes $t_{1/2(EtO\text{-}ibo\ turnover)}$
> 60 min

-similar rate of noribogaine formation to ibogaine
-slope of metabolite formation 0.01506

49
-continued

Noribogaine
(formed as metabolite)

The greater steric bulk of the Et does not affect the metabolic conversion of the compounds, however, the deuteration of the methyl group does have an unexpectedly superior effect.

The results obtained from an in vivo pharmacokinetic study in male Wistar rats correlates with the initial in vitro observations (rat liver microsome stability study). Following a single intraperitoneal dose of $CD_3O$-ibogamine, the detected maximum brain concentration level of this compound was only ~43% that of the ibogaine concentration detected after its administration, while the individual plasma concentrations differed by approximately 25% (lower for $CD_3O$-ibogamine). The maximum concentration of noribogaine (a common metabolite of both administered drugs) was comparable in the brain tissue (within 10% difference), while the noribogaine plasma concentration detected after $CD_3O$-ibogamine administration was only ~51% that of the concentration produced by ibogaine administration.

As observed in the in vitro study, $CD_3O$-ibogamine is metabolized faster than ibogaine, but the total amount of noribogaine produced is comparable within a short incubation period (~5 min) for both compounds. This indicates that $CD_3O$-ibogamine is metabolized via a second pathway (to produce a distinct putative metabolite other than noribogaine), which competes with the metabolic process leading to noribogaine. In vivo this results in different relative ratios of ibogaine or $CD_3O$-ibogamine to noribogaine after administration of each drug. As demonstrated recently (Rodriguez, P. et al. 2020), the relative amounts of ibogaine and noribogaine play an important role in therapeutic-like effects. Therefore, a suitable degree of deuterium labeling represents an important tool for adjusting the ratio of noribogaine and ibogaine species in plasma and brain, which in turn provides the possibility for increasing the therapeutic window.

For example, noribogaine has a lower tendency to produce adverse behavioral effects in comparison to ibogaine (Baumann, M. H. et al. 2020). It is therefore conceivable that administering such compound will achieve comparable therapeutic effects while shortening the duration of the psychedelic (altered) state and or mitigate the acute physical adverse effects such as ataxia. Moreover, a lower circulating noribogaine concentration in plasma (relative to brain) may decrease the cardiotoxicity risk.

REFERENCES

Alper, K. R. et al. *Am J Addict* 8, 234-242 (1999).
Alper, K. R. Ibogaine: A Review. *Alkaloids Chem Biol* 56, 1-38 (2001).
Baumann, M. H. et al. *The Journal of Pharmacology and Experimental Therapeutics* 297, 531-539 (2001).
Baumann, M. H. et al. *Ann. N. Y. Acad. Sci.* 914(1), 354-368 (2000).
Belgers, M. et al. *Transl Psychiatry* 6, e826 (2016).
Bhargava, H. N. & Cao, Y-J. *Brain Research* 771, 343-346 (1997).

50

Brown, T. K. & Alper, K. *Am J Drug Alcohol Abuse* 44, 24-36 (2018).
Brown, T. K. et al. *J Psychoactive Drugs* 51, 155-165, (2019).
He, D-Y. et al. *The Journal of Neuroscience* 25(3) 619-628 (2005).
Gash, D. M. et al. *Nature* 380, 252-255 (1996)
Glick, S. D. et al. *Alkaloids Chem Biol* 56, 39-53 (2001).
Glue, P. et al. *Clinical Pharmacology in Drug Development* 5(6), 460-468 (2016).
Glue, P. et al. *The Journal of Clinical Pharmacology* 55(6), 680-687 (2015).
Gonzalez, J. et al. *Front. Pharmacol.* 9, 374 (2018).
Kroupa, P. K. & Wells, H. MAPS, XV(2), 21-24 (2005).
Marton, S. et al. *Front. Pharmacol.* 10, 193 (2019)
Mash, D. C. et al. *Ann N Y Acad Sci* 844, 274-292 (1998).
Mash, D. C. et al. *Ann N Y Acad Sci* 914, 394-401 (2000).
Mash, D. C. et al. *J Psychopharmacol* 30, 688-697 (2016).
Mash, D. C. et al. *Front Pharmacol* 9, 529 (2018).
Naranjo, C. The Healing Journey. (Random House, 1973).
Noller, G. E. et al. *Am J Drug Alcohol Abuse* 44, 37-46 (2018).
Rodriguez, P. et al. *ACS Chem. Neurosci.* 11(11), 1661-1672 (2020).
Rubi, L. et al. *Cardiovascular Toxicology* 17, 215-218 (2017).
Schenberg, E. E. et al. *J Psychopharmacol* 28, 993-1000 (2014).
Schneider, J. A. & Sigg, E. B. *Ann N Y Acad Sci* 66, 765-776 (1957).
Sharma, S. S. & Bhargava, H. N. *Pharmacology* 57, 229-232 (1998).
Shear, M. K. et al. *Depress Anxiety* 28(2), 103-117 (2011).
Thoricatha, W. *Psychedelic Times* Jan. 28, 2020.

What is claimed is:

1. A composition comprising a mixture of deuterium containing and non-deuterium containing molecules having the structure:

wherein $R_1$ is wherein at least one of $H_1$, $H_2$ or $H_3$ is a deuterium-enriched —H site, and wherein in the mixture, the level of deuterium at any one of the deuterium-enriched —H sites is 20%-100%; or wherein at least one of $H_1$, $H_2$, $H_3$, $H_4$ or $H_5$ is a deuterium-enriched —H site, and wherein in the mixture, the proportion of molecules having deuterium at the at least one of $H_1$, $H_2$, $H_3$ $H_4$ or $H_5$ position is substantially greater than 0.0156% of molecules in the mixture, or a pharmaceutically acceptable salt of the compound.

2. The composition of claim 1, wherein $R_1$ is wherein at least one of $H_1$, $H_2$ or $H_3$ is a deuterium-enriched —H site.

3. The composition of claim 2, wherein each of $H_1$-$H_3$ are deuterium-enriched, wherein two of $H_1$-$H_3$ are deuterium-enriched, or wherein one of $H_1$-$H_3$ is deuterium-enriched.

4. The composition of claim 3, wherein the proportion of molecules having deuterium at each of the $H_1$-$H_3$ positions is substantially greater than 90% of molecules in the composition, wherein the proportion of molecules having deuterium at two of the $H_1$-$H_3$ positions is substantially greater than 90% of molecules in the composition, or wherein the proportion of molecules having deuterium at one of the $H_1$-$H_3$ positions is substantially greater than 90% of molecules in the composition.

5. The composition of claim 1, wherein $R_1$ is wherein (a) at least one of $H_1$, $H_2$, $H_3$, $H_4$ or $H_5$ is a deuterium-enriched —H site;

(b) each of $H_1$-$H_5$ are deuterium-enriched;

(c) each of $H_1$-$H_3$ are deuterium-enriched;

(d) each of $H_4$-$H_5$ are deuterium-enriched; or (e) one of $H_4$-$H_5$ is deuterium-enriched.

6. The composition of claim 5, wherein the proportion of molecules having deuterium at each of the $H_1$-$H_5$ positions is substantially greater than 90% of molecules in the composition, wherein the proportion of molecules having deuterium at each of the $H_1$-$H_3$ positions is substantially greater than 90% of molecules in the composition, or wherein the proportion of molecules having deuterium at each of the $H_4$-$H_5$ positions is substantially greater than 90% of molecules in the composition, or the proportion of molecules having deuterium at one of the $H_4$-$H_5$ positions is substantially greater than 90% of molecules in the composition.

7. The composition of claim 1, wherein $R_1$ is wherein each of $H_1$-$H_3$ are deuterium-enriched, and wherein the proportion of molecules having deuterium at each of the $H_1$-$H_3$ positions is substantially greater than 90% of molecules in the composition.

8. The composition of claim 1 wherein the deuterium containing molecules has the structure:

wherein D represents a deuterium-enriched —H site, or a pharmaceutically acceptable salt thereof.

9. A composition comprising a carrier and a compound having the structure:

wherein R$_1$ is wherein at least one of H$_1$, H$_2$ or H$_3$ is a deuterium-enriched —H site, or wherein at least one of H$_1$, H$_2$, H$_3$, H$_4$ or H$_5$ is a deuterium-enriched —H site, wherein the level of deuterium at any one of the deuterium-enriched —H sites of the deuterium containing molecules is no less than 50%, or a pharmaceutically acceptable salt of the compound.

10. The composition of claim 9, wherein R$_1$ is wherein at least one of H$_1$, H$_2$ or H$_3$ is a deuterium-enriched —H site.

11. The composition of claim 1, wherein the level of deuterium at any one of the deuterium-enriched —H sites of the deuterium containing molecules is 50%-100%, 70%-100%, 90%-100%, 97%-100%, or 99%-100%, or wherein the level of deuterium at any one of the deuterium-enriched —H sites of the deuterium containing molecules is no less than 50%, no less than 70%, no less than 90%, no less than 97% or no less than 99%.

12. A pharmaceutical composition comprising the composition of claim 1 and a pharmaceutically acceptable carrier.

13. The pharmaceutical composition of claim 12, further comprising a mu-opioid receptor agonist, an opioid or opiate.

14. The pharmaceutical composition of claim 13, wherein the opioid or opiate is morphine, hydromorphone, oxymorphone, codeine, dihydrocodeine, hydrocodone, oxycodone, nalbuphine, butorphanol, etorphine, dihydroetorphine, levorphanol, metazocine, pentazocine, meptazinol, meperidine (pethidine), fentanyl, sufentanil, alfentanil, buprenorphine, methadone, tramadol, tapentadol, mitragynine, 3-deutero-mitragynine, 7-hydroxymitragynine, 3-deutero-7-hydroxymitragynine, mitragynine pseudoindoxyl, tianeptine, 7-((3-bromo-6-methyl-5,5-dioxido-6,11-dihydrodibenzo[c,f][1,2]thiazepin-11-yl)amino)heptanoic acid, 7-((3-iodo-6-methyl-5,5-dioxido-6,11-dihydrodibenzo[c,f][1,2] thiazepin-11-yl)amino)heptanoic acid, 5-((3-bromo-6-methyl-5, 5-dioxido-6,11-dihydrodibenzo[c,f][1,2]thiazepin-11-yl) amino)pentanoic acid or 5-((3-iodo-6-methyl-5,5-dioxido-6, 11-dihydrodibenzo[c,f][1,2]thiazepin-11-yl)amino) pentanoic acid.

15. A method of (a) altering the psychological state of a subject comprising administering to the subject the composition of claim 1 comprising an effective amount of the mixture so as to thereby alter the psychological state of the subject;

(b) enhancing the effect of psychotherapy in a subject comprising administering to the subject the composition of claim 1 comprising an effective amount of the mixture so as to thereby enhance the effect 41 psychotherapy in the subject; or (c) inducing wakefulness or decreasing sleepiness in a subject comprising administering to the subject the composition of claim 1 comprising an effective amount of the mixture so as to thereby induce wakefulness or decrease sleepiness in the subject; or (d) inducing a stimulating effect in a subject comprising administering to the 1 subject the composition of claim comprising an effective amount of the mixture so as to thereby induce the stimulating effect in the subject.

16. The method of claim 15, wherein the subject is afflicted with a substance use disorder, wherein the substance use disorder is opioid use disorder, alcohol use disorder or stimulant use disorder.

17. A method of (a) treating a subject afflicted with opioid withdrawal symptoms comprising administering to the subject the composition of claim 1 comprising an effective amount of the mixture so as to thereby treat the subject afflicted with the opioid withdrawal symptoms; or (b) treating a subject afflicted with a depressive disorder, a mood disorder, an anxiety disorder, Parkinson's disease, or traumatic brain injury comprising administering to the subject the composition of claim 1 comprising an effective amount of the mixture so as to thereby treat the subject afflicted with the depressive disorder, the mood disorder, the anxiety disorder, Parkinson's disease or the traumatic brain injury, (c) treating a subject afflicted with substance use disorder comprising administering to the subject the composition of claim 1 comprising an effective amount of the mixture so as to thereby treat the subject afflicted with the substance use disorder, or (d) treating a subject afflicted with pain comprising administering to the subject composition of claim 1 comprising an effective amount of the mixture and the opioid or opiate so as to thereby treat the subject afflicted with pain.

18. A method for systemic in vivo delivery of a first compound having the structure:

to a subject, the method comprising administering to the subject a composition which comprises a carrier and a second compound having the structure:

wherein $R_1$ is wherein at least one of $H_1$, $H_2$ or $H_3$ is a deuterium-enriched —H site; and wherein the level of deuterium at any one of the deuterium-enriched —H sites is 20%-100%, or wherein at least one of $H_1$, $H_2$, $H_3$, $H_4$ or $H_5$ is a deuterium-enriched —H site,
or a pharmaceutically acceptable salt of the compound, so as to thereby deliver the first compound to the subject.

19. The method of claim 18, wherein the first compound is delivered at a rate that is substantially less than the rate of delivery of the second compound.

20. The composition of claim 8, wherein the deuterium containing molecules has the structure:

wherein D represents a deuterium-enriched —H site, or a pharmaceutically acceptable salt thereof.

* * * * *